US006858581B2

(12) United States Patent
Kuhner et al.

(10) Patent No.: US 6,858,581 B2
(45) Date of Patent: Feb. 22, 2005

(54) CHEMICALLY-MODIFIED PEPTIDES, COMPOSITIONS, AND METHODS OF PRODUCTION AND USE

(75) Inventors: Carla H. Kuhner, Avondale, PA (US); James A. Romesser, Kennett Square, PA (US)

(73) Assignee: Arizona State University, Tempe, AZ (US)

( * ) Notice: Subject to any disclaimer, the term of this patent is extended or adjusted under 35 U.S.C. 154(b) by 0 days.

(21) Appl. No.: 09/882,781

(22) Filed: Jun. 15, 2001

(65) Prior Publication Data

US 2003/0050247 A1 Mar. 13, 2003

Related U.S. Application Data

(60) Provisional application No. 60/212,441, filed on Jun. 16, 2000.

(51) Int. Cl.[7] .......................... A01N 37/18; A61K 38/00; C07K 14/00
(52) U.S. Cl. .................... 514/2; 260/998.2; 260/998.22; 530/300
(58) Field of Search ............................ 514/2; 530/300; 260/998.2, 998.22

(56) References Cited

U.S. PATENT DOCUMENTS

| | | | |
|---|---|---|---|
| 3,265,682 A | 8/1966 | Vogler et al. | |
| 4,448,715 A | 5/1984 | Ryan et al. | |
| 5,440,016 A | 8/1995 | Blondelle et al. | ........... 530/330 |
| 5,504,190 A | 4/1996 | Houghten et al. | |
| 5,512,549 A | 4/1996 | Chen et al. | |
| 5,654,451 A | 8/1997 | Kari | |
| 5,939,086 A | 8/1999 | Levy | |
| 6,126,939 A | * 10/2000 | Eisenbach-Schwartz et al. | 424/185.1 |

FOREIGN PATENT DOCUMENTS

| | | |
|---|---|---|
| EP | 0 280 610 A1 | 8/1988 |
| EP | 0 618 225 A1 | 10/1994 |
| ES | 8702346 A1 | 3/1987 |
| ES | 2020148 A6 | 7/1991 |
| GB | 1 237 918 A | 7/1971 |
| JP | HEI 8-176190 | 7/1996 |
| WO | 92/01462 A1 | 2/1992 |
| WO | 95/19370 A1 | 7/1995 |
| WO | 96/40768 A2 A3 | 12/1996 |
| WO | 98/07745 A2 A3 | 2/1998 |
| WO | 99/14231 A2 A3 | 3/1999 |
| WO | 99/37667 A1 | 7/1999 |
| WO | 00/00214 A2 A3 | 1/2000 |
| WO | WO 00/59527 | 10/2000 |

OTHER PUBLICATIONS

Dabrowska, M. et al., "Derivatives of the L–Lysine–Peptides with Antibacterial Activity", *Pol. J. Pharmacol Pharm*, 1976, 28(1), 77–88, XP–008004973.

Kikumoto, R. et al.,"Thrombin Inhibitors. 2. Amide Derivatives of Nα–Substituted L–Arginine", *Journal of Medicinal Chemistry, American Chemical Society*, US, 1980, 23(8), 830–836, XP 001008617.

Sugimoto, Y. et al., "Influence of Chemical Modification of N alpha–cocoyl–Larginine Ethyl Ester on its Hepatitis B Surface Antigen–Inactivating Effect", *Antimicrobial Agents and Chemotheraphy*, 1980, 18(4), 525–528, XP 002203217.

Perez, L. et al., "Synthesis Aggregation and Biological Properties of a New Class of Gemini Cationic Amphiphilic Compounds from Arginine Bis(ARGS)", *Langmuir*, 1996, 12(22), 5296–5301, XP–002203216.

Nakamura, H. et al., "Antibacterial Activity of Amphipathic Basic Peptides with a Long Acyl Group and Their Interaction with Phospholipid Bilayers," *Bull Chem Soc Jpn*, Apr. 1, 1990, 63(4), 1180–1184.

International Search Report from corresponding PCT Application PCT/US01/19400; Date of Mailing: Oct. 2, 2002.

Falla T.J. et al., "Mode of action of the antimicrobial peptide indoicidin",1996, vol. 271 (32), pp 19298–19303.

Hancock,R E.W.,"The therapeutic potential of cationic peptides" *Exp. Opin. Invest. Drugs*, 1998, 7(2), pp 167–174.

Hancock,R.E.W., et al., "Cationic bactericidal peptides" *Advances In Microbial Physiology*, 195, vol. 37, pp 135–175.

Hancock,R.E.W. et al., "Cationic peptides: a new source of antibiotics" *TiB Tech.*, 1998, 16, pp82–88.

Lehrer et al.,"Defensins: Natural peptide antibiotics from neutrophils" *ASM News*, 1990, 56, 315–318.

Merrifield,R.B.,"Solid phase peptide synthesis. I. The synthesis of a tetrapeptide" *J. Amer. Chem Soc.*, 1963, 85, pp 2149–2154.

Nguyen–Dinh P., et al.,"Antiparasitic agents and suceptibility tests"*Manual of Clinical Microbiology*, 7th Edition, pp 1653–1662.

Oh et al.,"Structure–activity relationship study:short antimicrobial peptides" *J. Peptide Res.*, 1998, 56, pp 41–46.

Wakabayashi et al.,"N–acylated and d enantiomer derivatives of a nonamer core peptide of lactoferricin b showing improved antimicrobial activity" *Antimicrobial Agents and Chemotherapy*, 1999, 43, 1267–1269.

"A formulary of cosmetic preparations" vol. 2, Chapters 7–16, pp 5–484.

(List continued on next page.)

*Primary Examiner*—Mark Navarro
(74) *Attorney, Agent, or Firm*—Christine, Meis, McAuliffle, Esq.; Jennings, Strouss and Salmon, PLC

(57) ABSTRACT

Compositions and methods for inhibiting and controlling the growth of microbes are disclosed. The composition comprises at least one chemically-modified peptide with antimicrobial activity and at least one carrier. The method comprises of administering an amount, effective for the prevention, inhibition and termination of microbial growth for industrial, pharmaceutical, household and personal care use.

8 Claims, 3 Drawing Sheets

OTHER PUBLICATIONS

Goodman & Gilman's:*The Pharmacological Basis of Therapeutics* (8$^{th}$ edition), pp 1–83.

Gutte B., "*Peptides: Synthesis, Structures and Applications*" 1995.

Lloyd–Williams et al., "*Chemical approaches to the synthesis of peptides and proteins*"1997.

Remington's Pharmaceutical Sciences (part 8), pp 1435–1694.

The CFTA Cosmetic Ingredient Handbook, 1992, 2$^{nd}$ edition.

* cited by examiner

Figure 1

N-terminally modified peptides

| Sequence | MIC (µg/ml) | |
|---|---|---|
| | *K. pneumoniae* ATCC 10031 | *P. aeruginosa* ATCC 10145 |
| Butanoyl-RWF-NH$_2$ | 250 | 250 |
| Hexanoyl-RWF-NH$_2$ | 62 | 62 |
| Octanoyl-RWF-NH$_2$ | 8 | 15 |
| Decanoyl-RWF-NH$_2$ | 8 | 8 |
| Stearoyl-RWF-NH$_2$ | 500 | 500 |
| (α-Stearoyl, γ-stearoyl-K)-RWF-NH$_2$ | >500 | >500 |
| (α-Octanoyl, γ-octanoyl-K)-RWF-NH$_2$ | 8 | 31 |
| Naphthoyl-RWF-NH$_2$ | 15 | 62 |
| Naphthylacetyl-RWF-NH$_2$ | 15 | 15 |
| Octanoyl-RWC-NH$_2$ (Monomer) | 8 | 15 |
| Octanoyl-RWC-NH$_2$ (Dimer) | 4 | 15 |
| Octanoyl-RW-NH-CH$_2$-C$_6$H$_5$ | 62 | 62 |
| (α[α-Octanoyl-RW, γ-octanoyl-RW]-K)-NH$_2$ | 4 | 8 |
| Octanoyl-RW-NH$_2$ | 15 | 8 |
| Octanoyl-RF-NH$_2$ | 500 | 500 |
| Octanoyl-RC-NH$_2$ | 62 | 250 |
| Octanoyl-RY-NH$_2$ | 500 | >500 |
| Octanoyl-RW-OH | >500 | >500 |
| Octanoyl-R-NH-CH$_2$-C$_6$H$_5$ | 250 | 125 |
| Octanoyl-R-NH$_2$ | >500 | >500 |
| Octanoyl-W-OH | >500 | >500 |

Figure 2

N- and C-terminally modifed peptides

| Sequence | MIC (μg/ml) | |
|---|---|---|
| | K. pneumoniae ATCC 10031 | P. aeruginosa ATCC 10145 |
| Octanoyl-NH-octyl | 125 | 250 |
| Octanoyl-R-NH-octyl | 4 | 4 |
| Octanoyl-G-NH-octyl | >500 | >500 |
| Octanoyl-H-NH-octyl | >500 | >500 |
| Octanoyl-K-NH-octyl | 15 | 15 |
| Heptanoyl-R-NH-heptyl | 31 | 15 |
| Nonanoyl-R-NH-nonyl | 2 | 4 |
| Decanoyl-R-NH-decyl | 4 | 15 |
| Octanoyl-RA-NH-octyl | 15 | 8 |
| Octanoyl-RC-NH-octyl | 8 | 15 |
| Octanoyl-RF-NH-octyl | 8 | 8 |
| Octanoyl-RG-NH-octyl | 8 | 8 |
| Octanoyl-RH-NH-octyl | 8 | 2 |
| Octanoyl-HR-NH-octyl | 15 | 4 |
| Octanoyl-RK-NH-octyl | 125 | 15 |
| Octanoyl-RL-NH-octyl | 8 | 8 |
| Octanoyl-RN-NH-octyl | 62 | 8 |
| Octanoyl-RQ-NH-octyl | 15 | 8 |
| Octanoyl-RR-NH-octyl | 4 | 4 |
| Octanoyl-RW-NH-octyl | 125 | 125 |
| Octanoyl-RY-NH-octyl | 8 | 8 |
| Octanoyl-RRR-NH-octyl | 8 | 4 |
| Butanoyl-RG-NH-butyl | >500 | >500 |
| Hexanoyl-RG-NH-hexyl | >500 | >500 |
| Hexanoyl-RR-NH-hexyl | 125 | 62 |
| Heptanoyl-RR-NH-heptyl | 31 | 15 |
| Nonanoyl-RR-NH-nonyl | 2 | 2 |
| Decanoyl-RR-NH-decyl | 4 | 4 |
| Butanoyl-RR-NH-octyl | 250 | 125 |
| Hexanoyl-RR-NH-octyl | 31 | 15 |
| Octanoyl-RR-NH-hexyl | 31 | 4 |
| Octanoyl-RR-NH-butyl | 250 | 31 |
| Benzoyl-RR-NH-benzyl | 500 | 500 |
| Octanoyl-KK-NH-octyl | 62 | >500 |
| Octanoyl-KW-NH-octyl | >500 | >500 |
| Octanoyl-KG-NH-octyl | >500 | >500 |
| Octanoyl-KR-NH-octyl | 4 | 2 |
| Octanoyl-FF-NH-octyl | >500 | >500 |
| Octanoyl-HH-NH-octyl | >500 | >500 |
| Octanoyl-LL-NH-octyl | >500 | >500 |
| Octanoyl-RFFR-NH-octyl | 4 | 4 |

Figure 3

Diacyl Peptides vs. Clinical Organisms

| Organism | MIC (µg/ml) | | | | | |
|---|---|---|---|---|---|---|
| | Octanoyl-R-NH-octyl | Octanoyl-KR-NH-octyl | Octanoyl-RR-NH-octyl | Nonanoyl-R-NH-octyl | Nonanoyl-R-NH-nonyl | Decanoyl-RR-NH-decyl |
| B. cepacia ATCC 25416 | >125 | >125 | >125 | >125 | >125 | >125 |
| E. coli ATCC 25922 | 7.8 | 3.9 | 3.9 | 3.9 | 3.9 | 3.9 |
| K. pneumoniae ATCC 10031 | 3.9 | 3.9 | 3.9 | 3.9 | 2 | 3.9 |
| K. pneumoniae ATCC 27736 | 31.3 | 62.5 | 31.3 | 31.3 | 3.9 | 3.9 |
| P. aeruginosa ATCC 10145 | 7.8 | 3.9 | 3.9 | 3.9 | 3.9 | 3.9 |
| P. aeruginosa ATCC 27853 | 7.8 | 3.9 | 2 | 2 | 3.9 | 3.9 |
| P. aeruginosa FRD1 | 15.6 | 7.8 | 3.9 | 3.9 | 7.8 | 7.8 |
| S. aureus ATCC 29213 | 3.9 | 3.9 | 3.9 | 3.9 | 2 | 2 |
| S. aureus (MRSA) ATCC 33591 | 3.9 | 3.9 | 2 | 2 | 2 | 2 |
| S. sanguis ATCC 10556 | 7.8 | 15.6 | 7.8 | 7.8 | 4 | 2 |
| S. mutans ATCC 25175 | 3.9 | | 3.9 | 3.9 | 3.9 | 3.9 |
| C. albicans ATCC 10231 | 3.9 | 31.3 | 31.3 | 31.3 | 2 | 62.5 |

CHEMICALLY-MODIFIED PEPTIDES, COMPOSITIONS, AND METHODS OF PRODUCTION AND USE

This Application: claims benefit of U.S. provisional Application Ser. No. 60/212,441 filed Jun. 16, 2000.

BACKGROUND OF THE INVENTION

1. Field of the Invention

This invention relates to chemically-modified peptides having antimicrobial activity and methods of making them and using them to combat microorganisms. Chemically-modified peptides of the present invention are useful in treatment of industrial aqueous systems as well as pharmaceuticals to treat clinically relevant diseases for mammals, plants, avian and aquatic organisms, but their application is not limited thereto.

2. Background of the Invention and Related Information

Peptides are now recognized as part of a global defense mechanism used by animals and plants in terrestrial and marine environments to prevent microbial attack. The discovery of antimicrobial peptides has generated interest in the use of these compounds to combat clinically relevant microorganisms, in particular, multi-drug resistant organisms. Large screening programs have been developed to identify potential peptide-based drug candidates from both natural product-and combinatorial chemistry-derived libraries. Antimicrobial peptides are also potential candidates for the prevention of biofouling in industrial water systems, where they would represent a novel chemical class of antibiofouling compounds.

Peptides are produced naturally in bacteria, fungi, plants, insects, amphibians, crustaceans, fish and mammals [Hancock, Advances in Microbial Physiology, 135–175, Academic Press (1995)]. They represent a major inducible defense against microbes and their production in the immune system of many species is controlled by transcriptional elements. For instance, in humans, antimicrobial peptides are found in neutrophils which are responsible for responding against invasion of foreign organisms [Lehrer et al. ASM News, 56, 315–318, (1990)]. Natural antimicrobial peptides have a moderate spectrum of activity against microbes and are usually present in moderate amounts. Natural antimicrobial peptides of 12–50 amino acid residues have been obtained in the past 20 years via isolation from the defense systems of insects, amphibians and mammals [Oh et al. J. Peptide Res., 56, 41–46, (1998)]. Use of these peptides in clinical trials has shown effective antimicrobial activity [Hancock, Exp. Opin. Invest. Drugs, 7, 167–174, (1998)].

Treatment of microorganisms with antibiotics has resulted in inadequate inhibition of bacterial growth due to resistance. Peptides have shown excellent activity against antibiotic resistant microorganisms in vitro [Hancock and Lehrer, TiB Tech., 16, 82–88, (1998)].

The charge distribution and hydrophobic properties of a peptide appear to be important factors in determining its effectiveness. The peptides are usually large (12–50 amino acids) and said to be cationic due to the presence of positively charged basic amino acid residues such as arginine and lysine [Hancock, Exp. Opin. Invest. Drugs, 7, 167–174, (1998)]. It is suggested that the cationicity of the peptide may play an important role in the peptide interaction with negatively charged membranes. For instance, cationic peptides are said to compete with divalent cations on the surface of Gram-negative bacteria and prevent their interaction with lipopolysaccharide (LPS) molecules [Hancock, Exp. Opin. Invest. Drugs, 7, 167–174, (1998)]. It is hypothesized that the displacement of divalent cations by cationic peptides creates a distortion in the outer membrane of the bacteria through which peptides may pass.

Industrial facilities employ many methods of preventing biofouling of industrial water systems. Many microbial organisms are involved in biofilm formation in industrial waters. Growth of slime-producing bacteria in industrial water systems causes problems including decreased heat transfer, fouling and blockage of lines and valves, and corrosion or degradation of surfaces. Control of bacterial growth in the past has been accomplished with biocides. Many biocides and biocide formulations are known in the art. However, many of these contain components which may be environmentally deleterious or toxic, and are often resistant to breakdown.

The manufacturing cost of peptides may be a limiting factor in their antimicrobial application [Hancock and Lehrer, TiB Tech., 16, 82–88, (1998)]. The long chain length of the natural antimicrobial peptides is a major factor contributing to their cost of synthesis.

U.S. Pat. No. 5,504,190 describes a process for solid-support synthesis of equimolar oligomer mixtures that prevents unequal reaction yields during addition of blocked amino acids and allows for equal and precise representation of amino acid residues along the chain of the peptide. A hexapeptide library is described which contains 64,000,000 peptides. The peptides can be modified with a $C_1$–$C_8$ N-terminal acyl group. N-terminally acetylated hexa- and heptapeptides are described which are said to exhibit antimicrobial activity.

Another U.S. Pat. No. 5,512,549 discloses a peptide having 29 amino acid residues and modified with a $C_6$–$C_{10}$ acyl chain which is said to be useful in the treatment of non-insulin dependent diabetes mellitus. The peptides are not said to exhibit antimicrobial activity.

Antimicrobial activity of N-acylated derivatives of an arginine, lysine and tryptophan rich segment of lactoferricin B has been described [Wakabayashi et al, Antimicrobial Agents and Chemotherapy, 43, 1267–1269, (1999)]. Acyl chains were 6 to 10 carbons long; C-10 giving optimal activity against *Escherchia coli, Pseudomonas aeruginosa* and *Staphylococcus aureus*.

The present invention satisfies the need in the art with short-chained peptides which are easier to produce and have effective antimicrobial activity.

SUMMARY OF THE INVENTION

The invention provides chemically-modified antimicrobial peptides represented by Formula I:

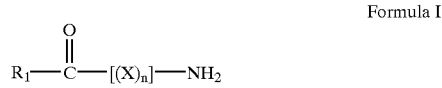

Formula I wherein:
X is any natural or non-natural, modified or unmodified amino acid except glutamate or aspartate;
n=1 to 5;
wherein:
(a) when n=1, then
said peptide comprises a cationic amino acid;
the charge of said peptide at neutral pH is at least 1;
$R^1$ is $C^1$–$C_{20}$ alkyl; $C_3$–$C_6$ cycloalkyl; $C_4$–$C_{20}$ alkenyl; $C_4$–$C_{20}$ alkynyl; $C_1$–$C_{20}$ haloalkyl; (semi-color)

$C_3$–$C_{20}$ haloalkenyl; $C_3$–$C_{20}$ haloalkynyl; $C_2$–$C_{20}$ alkoxyalkyl; $C_2$–$C_{20}$ alkylthioalkyl; $C_2$–$C_{20}$ alkylsulfinylalkyl; $C_2$–$C_{20}$ alkylsulfonylalkyl; $C_5$–$C_{20}$ cycloalkylalkyl; $C_4$–$C_{20}$ alkenyloxyalkyl; $C_4$–$C_{20}$ alkynyloxyalkyl; $C_4$–$C_{20}$ (cycloalkyl)oxyalkyl; $C_4$–$C_{20}$ alkenylthioalkyl; $C_4$–$C_{20}$ alkynylthioalkyl; $C_6$–$C_{20}$ (cycloalkyl)thioalkyl; $C_2$–$C_{20}$ haloalkoxyalkyl; $C_4$–$C_{20}$ haloalkenyloxyalkyl; $C_4$–$C_{20}$ haloalkynyloxyalkyl; $C_4$–$C_{20}$ alkoxylalkenyl; $C_4$–$C_{20}$ alkoxyalkynyl; $C_4$–$C_{20}$ alkylthioalkenyl; $C_4$–$C_{20}$ alkylthioalkynyl; $C_4$–$C_{20}$ trialkylsilylalkyl; $C_1$–$C_{20}$ alkyl substituted with $NR_3R_4$, nitro, cyano, or phenyl optionally substituted with $R_5$, $R_6$, and $R_7$; $C_1$–$C_{20}$ alkoxy; $C_1$–$C_{20}$ haloalkoxy; $C_1$–$C_{20}$ alkylthio; $C_1$–$C_{20}$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;

$R_3$ is independently hydrogen; $C_1$–$C_4$ alkyl; or phenyl optionally substituted with at least one $R_8$;

$R_4$ is independently hydrogen; $C_1$–$C_8$ alkyl; or phenyl optionally substituted with at least one $R_8$;

$R_5$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R_8$; cyano; nitro; $C_1$–$C_6$ haloalkoxy; $C_1$–$C_6$ haloalkythio; $C_2$–$C_6$ alkenyl; $C_2$–$C_6$ haloalkenyl; acetyl; $CO_2CH_3$; or $N(C_1$–$C_2$ alkyl$)_2$;

$R_6$ is independently methyl; ethyl; methoxy; methylthio; halogen; or trifluoromethyl;

$R_7$ is independently halogen; and $R_8$ is independently halogen; $C_1$–$C_4$ alkyl; $C_1$–$C_4$ alkoxy; $C_1$–$C_4$ haloalkyl; nitro; or cyano;

(b) when n=2 or 3, then at least one of the amino acids are cationic amino acids; the net charge of said peptide at neutral pH is at least +1;

$R_1$ is $C_1$–$C_9$ alkyl; $C_3$–$C_6$ cycloalkyl; $C_4$–$C_9$ alkenyl; $C_4$–$C_9$ alkynyl; $C_1$–$C_9$ haloalkyl; $C_3$–$C_9$ haloalkenyl; $C_3$–$C_9$ haloalkynyl; $C_2$–$C_9$ alkoxyalkyl; $C_2$–$C_9$ alkylthioalkyl; $C_2$–$C_9$ alkylsulfinylalkyl; $C_2$–$C_9$ alkylsulfonylalkyl; $C_5$–$C_9$ cycloalkylalkyl; $C_4$–$C_9$ alkenyloxyalkyl; $C_4$–$C_9$ alkynyloxyalkyl; $C_4$–$C_9$ (cycloalkyl)oxyalkyl; $C_4$–$C_9$ alkenylthioalkyl; $C_4$–$C_9$ alkynylthioalkyl; $C_6$–$C_9$ (cycloalkyl)thioalkyl; $C_2$–$C_9$ haloalkoxyalkyl; $C_4$–$C_9$ haloalkenyloxyalkyl; $C_4$–$C_9$ haloalkynyloxyalkyl; $C_4$–$C_9$ alkoxylalkenyl; $C_4$–$C_9$ alkoxyalkynyl; $C_4$–$C_9$ alkylthioalkenyl; $C_4$–$C_9$ alkylthioalkynyl; $C_4$–$C_9$ trialkylsilylalkyl; $C_1$–$C_9$ alkyl substituted with $NR_3R_4$, nitro, cyano, or phenyl optionally substituted with $R_5$, $R_6$, and $R_7$; $C_1$–$C_9$ alkoxy; $C_1$–$C_9$ haloalkoxy; $C_1$–$C_9$ alkylthio; $C_1$–$C_9$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;

$R_3$ is independently hydrogen; $C_1$–$C_4$ alkyl; or phenyl optionally substituted with at least one $R_8$;

$R_4$ is independently hydrogen; $C_1$–$C_8$ alkyl; or phenyl optionally substituted with at least one $R_8$;

$R_5$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R_8$; cyano; nitro; $C_1$–$C_6$ haloalkoxy; $C_1$–$C_6$ haloalkythio; $C_2$–$C_6$ alkenyl; $C_2$–$C_6$ haloalkenyl; acetyl; $CO_2CH_3$; or $N(C_1$–$C_2$ alkyl$)_2$;

$R_6$ is independently methyl; ethyl; methoxy; methylthio; halogen; or trifluoromethyl;

$R_7$ is independently halogen; and $R_8$ is independently halogen; $C_1$–$C_4$ alkyl; $C_1$–$C_4$ alkoxy; $C_1$–$C_4$ haloalkyl; nitro; or cyano;

(c) when n=4 or 5, then at least two of the amino acids are cationic amino acids; the net charge of the peptide at neutral pH is at least +2;

$R_1$ is $C_1$–$C_{20}$ alkyl; $C_3$–$C_6$ cycloalkyl; $C_4$–$C_{20}$ alkenyl; $C_4$–$C_{20}$ alkynyl; $C_1$–$C_{20}$ haloalkyl; $C_3$–$C_{20}$ haloalkenyl; $C_3$–$C_{20}$ haloalkynyl; $C_2$–$C_{20}$ alkoxyalkyl; $C_2$–$C_{20}$ alkylthioalkyl; $C_2$–$C_{20}$ alkylsulfinylalkyl; $C_2$–$C_{20}$ alkylsulfonylalkyl; $C_5$–$C_{20}$ cycloalkylalkyl; $C_4$–$C_{20}$ alkenyloxyalkyl; $C_4$–$C_{20}$ alkynyloxyalkyl; $C_4$–$C_{20}$ (cycloalkyl)oxyalkyl; $C_4$–$C_{20}$ alkenylthioalkyl; $C_4$–$C_{20}$ alkynylthioalkyl; $C_6$–$C_{20}$ (cycloalkyl)thioalkyl; $C_2$–$C_{20}$ haloalkoxyalkyl; $C_4$–$C_{20}$ haloalkenyloxyalkyl; $C_4$–$C_{20}$ haloalkynyloxyalkyl; $C_4$–$C_{20}$ alkoxylalkenyl; $C_4$–$C_{20}$ alkoxyalkynyl; $C_4$–$C_{20}$ alkylthioalkenyl; $C_4$–$C_{20}$ alkylthioalkynyl; $C_4$–$C_{20}$ trialkylsilylalkyl; $C_1$–$C_{20}$ alkyl substituted with $NR_3R_4$, nitro, cyano, or phenyl optionally substituted with $R_5$, $R_6$, and $R_7$; $C_1$–$C_{20}$ alkoxy; $C_1$–$C_{20}$ haloalkoxy; $C_1$–$C_{20}$ alkylthio; $C_1$–$C_{20}$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;

$R_3$ is independently hydrogen; $C_1$–$C_4$ alkyl; or phenyl optionally substituted with at least one $R_8$;

$R_4$ is independently hydrogen; $C_1$–$C_8$ alkyl; or phenyl optionally substituted with at least one $R_8$;

$R_5$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R_8$; cyano; nitro; $C_1$–$C_6$ haloalkoxy; $C_{1-6}$ haloalkythio; $C_2$–$C_6$ alkenyl; $C_2$–$C_6$ haloalkenyl; acetyl; $CO_2CH_3$; or $N(C_1$–$C_2$ alkyl$)_2$;

$R_6$ is independently methyl; ethyl; methoxy; methylthio; halogen; or trifluoromethyl;

$R_7$ is independently halogen; and $R_8$ is independently halogen; $C_1$–$C_4$ alkyl; $C_1$–$C_4$ alkoxy; $C_1$–$C_4$ haloalkyl; nitro; or cyano.

At least one of the peptides of Formula I may be combined with at least one carrier to form an antimicrobial composition.

In some embodiments, the antimicrobial peptides and compositions thereof comprise 2 amino acids, wherein the N-terminal amino acid is a cationic amino acid and the C-terminal amino acid is any amino acid except glutamate or aspartate. For example, the antimicrobial peptides of two amino acids may be Arg-Trp, Lys-Trp, and Orn-Trp.

In other embodiments, the antimicrobial peptides and compositions thereof comprise three amino acids, such as, for example, Arg-Phe-Arg; Lys-Phe-Arg; Lys-Phe-Lys; Arg-Phe-Lys; Orn-Phe-Arg; Orn-Phe-Orn; Arg-Phe-Orn; Arg-Trp-Phe; Lys-Trp-Phe; Orn-Trp-Phe; Arg-Trp-Cys; Lys-Trp-Cys; Orn-Trp-Cys; Arg-Phe-Trp; Lys-Phe-Trp; Orn-Phe-Trp; Arg-Arg-Trp; Lys-Lys-Trp; Lys-Arg-Trp; Arg-Lys-Trp; Orn-Orn-Trp; Orn-Arg-Trp; Arg-Orn-Trp; Arg-Trp-Arg; Lys-Trp-Arg; Arg-Trp-Lys; Lys-Trp-Lys; Orn-Trp-Arg; Arg-Trp-Orn; and Orn-Trp-Orn.

In further embodiments, antimicrobial peptides and compositions thereof comprise four amino acids. Examples of such antimicrobial peptides include, but are not limited to those having sequences represented by SEQ ID NO:1; SEQ ID NO:2; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; and SEQ ID NO:23.

Other embodiments of the invention include antimicrobial peptides represented by Formula II:

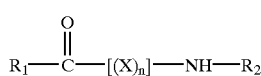

Formula II wherein:
- X is any natural or non-natural, modified or unmodified amino acid except glutamate or aspartate;
- n=1 to 10;
- $R_1$ is $C_1-C_{20}$ alkyl; $C_3-C_6$ cycloalkyl; $C_4-C_{20}$ alkenyl; $C_4-C_{20}$ alkynyl; $C_1-C_{20}$ haloalkyl; $C_3-C_{20}$ haloalkenyl; $C_3-C_{20}$ haloalkynyl; $C_2-C_{20}$ alkoxyalkyl; $C_2-C_{20}$ alkylthioalkyl; $C_2-C_{20}$ alkylsulfinylalkyl; $C_2-C_{20}$ alkylsulfonylalkyl; $C_5-C_{20}$ cycloalkylalkyl; $C_4-C_{20}$ alkenyloxyalkyl; $C_4-C_{20}$ alkynyloxyalkyl; $C_4-C_{20}$ (cycloalkyl)oxyalkyl; $C_4-C_{20}$ alkenylthioalkyl; $C_4-C_{20}$ alkynylthioalkyl; $C_6-C_{20}$ (cycloalkyl)thioalkyl; $C_2-C_{20}$ haloalkoxyalkyl; $C_4-C_{20}$ haloalkenyloxyalkyl; $C_4-C_{20}$ haloalkynyloxyalkyl; $C_4-C_{20}$ alkoxylalkenyl; $C_4-C_{20}$ alkoxyalkynyl; $C_4-C_{20}$ alkylthioalkenyl; $C_4-C_{20}$ alkylthioalkynyl; $C_4-C_{20}$ trialkylsilylalkyl; $C_1-C_{20}$ alkyl substituted with $NR_3R_4$, nitro, cyano, or phenyl optionally substituted with $R_5$, $R_6$, and $R_7$; $C_1-C_{20}$ alkoxy; $C_1-C_{20}$ haloalkoxy; $C_1-C_{20}$ alkylthio; $C_1-C_{20}$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;
- $R_2$ is $C_1-C_{20}$ alkyl; $C_3-C_6$ cycloalkyl; $C_4-C_{20}$ alkenyl; $C_4-C_{20}$ alkynyl; $C_1-C_{20}$ haloalkyl; $C_3-C_{20}$ haloalkenyl; $C_3-C_{20}$ haloalkynyl; $C_2-C_{20}$ alkoxyalkyl; $C_2-C_{20}$ alkylthioalkyl; $C_2-C_{20}$ alkylsulfinylalkyl; $C_2-C_{20}$ alkylsulfonylalkyl; $C_5-C_{20}$ cycloalkylalkyl; $C_4-C_{20}$ alkenyloxyalkyl; $C_4-C_{20}$ alkynyloxyalkyl; $C_4-C_{20}$ (cycloalkyl)oxyalkyl; $C_4-C_{20}$ alkenylthioalkyl; $C_4-C_{20}$ alkynylthioalkyl; $C_6-C_{20}$ (cycloalkyl)thioalkyl; $C_2-C_{20}$ haloalkoxyalkyl; $C_4-C_{20}$ haloalkenyloxyalkyl; $C_4-C_{20}$ haloalkynyloxyalkyl; $C_4-C_{20}$ alkoxylalkenyl; $C_4-C_{20}$ alkoxyalkynyl; $C_4-C_{20}$ alkylthioalkenyl; $C_4-C_{20}$ alkylthioalkynyl; $C_4-C_{20}$ trialkylsilylalkyl; $C_1-C_{20}$ alkyl substituted with $NR_3R_4$, nitro, cyano, or phenyl optionally substituted with $R_5$, $R_6$, and $R_7$; $C_1-C_{20}$ alkoxy; $C_1-C_{20}$ haloalkoxy; $C_1-C_{20}$ alkylthio; $C_1-C_{20}$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;
- $R_3$ is independently hydrogen; $C_1-C_4$ alkyl; or phenyl optionally substituted with at least one $R_8$;
- $R_4$ is independently hydrogen; $C_1-C_8$ alkyl; or phenyl optionally substituted with at least one $R_8$;
- $R_5$ is independently $C_1-C_6$ alkyl; $C_1-C_6$ alkoxy; $C_1-C_6$ haloalkyl; halogen; $C_2-C_8$ alkynyl; $C_1-C_6$ thioalkyl; phenyl or phenoxy each optionally substituted with at least one $R_8$; cyano; nitro; $C_1-C_6$ haloalkoxy; $C_1-C_6$ haloalkythio; $C_2-C_6$ alkenyl; $C_2-C_6$ haloalkenyl; acetyl; $CO_2CH_3$; or $N(C_1-C_2$ alkyl$)_2$;
- $R_6$ is independently methyl; ethyl; methoxy; methylthio; halogen; or trifluoromethyl;
- $R_7$ is independently halogen; and
- $R_8$ is independently halogen; $C_1-C_4$ alkyl; $C_1-C_4$ alkoxy; $C_1-C_4$ haloalkyl; nitro; or cyano.

In some embodiments, when the antimicrobial peptides are 1–3 amino acids, at least one amino acid is a cationic amino acid, and the net charge of said peptide at neutral pH is at least +1. In other embodiments, when the antimicrobial peptides are 4 amino acids, at least two of the amino acids are cationic amino acids, and the net charge of said peptide at neutral pH is at least +2. In other embodiments, when the antimicrobial peptides are 5–7 amino acids, at least three of the amino acids are cationic amino acids, and the net charge of the peptide at neutral pH is at least +3. In still other embodiments, when the peptides are 8–10 amino acids, at least four of the amino acids are cationic amino acids, and the net charge of the peptide at neutral pH is at least +4.

At least one of the peptides of Formula II may be combined with at least one carrier to form an antimicrobial composition.

In some embodiments the peptides and compositions thereof comprise a single amino acid, such as arginine, lysine or ornithine.

In other embodiments the peptides and compositions thereof comprises 2 amino acids wherein at least one of the amino acids is a cationic amino acid, and the other amino acid is any amino except glutamate or aspartate, and wherein the net charge of said peptide is at least +1. Non-limiting examples of such peptides include Arg-Arg; Arg-Phe; Arg-Tyr; Arg-Ala; Arg-Ile; Arg-Leu; Arg-Pro; Arg-Val; Arg-Cys; Arg-Met; Arg-Ser; Arg-Thr; Arg-Asn; Arg-Gln; Arg-Nal; Arg-His; Arg-Gly; Phe-Arg; Tyr-Arg; Ala-Arg; Ile-Arg; Leu-Arg; Pro-Arg; Val-Arg; Cys-Arg; Met-Arg; Ser-Arg; Thr-Arg; Asn-Arg; Gln-Arg; Nal-Arg; His-Arg; and Gly-Arg.

In other embodiments, the peptides and compositions thereof comprise three amino acids, including, but not limited to Arg-Arg-Arg; Arg-Phe-Arg; Arg-Tyr-Arg; Arg-Ala-Arg; Arg-Ile-Arg; Arg-Leu-Arg; Arg-Pro-Arg; Arg-Val-Arg; Arg-Cys-Arg; Arg-Met-Arg; Arg-Ser-Arg; Arg-Thr-Arg; Arg-Asn-Arg; Arg-Gln-Arg; Arg-Nal-Arg; Arg-Orn-Arg; Arg-His-Arg; Arg-Lys-Arg; Arg-Gly-Arg; Arg-Arg-Nal; Arg-Arg-Phe; Arg-Arg-Tyr; Arg-Arg-Ala; Arg-Arg-Ile; Arg-Arg-Leu; Arg-Arg-Pro; Arg-Arg-Val; Arg-Arg-Cys; Arg-Arg-Met; Arg-Arg-Ser; Arg-Arg-Thr; Arg-Arg-Asn; Arg-Arg-Gln; Arg-Arg-Lys; Arg-Arg-His; Arg-Arg-Orn; and Arg-Arg-Gly.

The antimicrobial peptides of the invention may be incorporated into a polymer, such as, for example, a polysaccharide, a glycol polymer, a polyester, a polyurethane, a polyacrylate, a polyacrylonitrile, a polyamide, a polyolefin, a polystyrene, a vinyl polymer, a polypropylene, silk, a biopolymer, and mixtures thereof.

The antimicrobial compositions of the invention comprise at least one carrier, such as, for example, a pharmaceutically acceptable carrier, an industrially acceptable carrier, a household product, paint, joint cement, or a personal care composition.

In the antimicrobial compositions of the invention, the peptides are typically present in an amount of about 0.000001 to about 99%. In other embodiments, the peptides are present in an amount of about 0.001 to about 50%. In other embodiment, the peptides are present in an amount of about 0.01 to about 25%.

In the antimicrobial compositions of the invention, the carrier, or mixture of carriers, is typically present in an amount of about 1 to about 99% by weight of the composition. In other embodiments, the carrier, or mixture of carriers, is typically present in an amount of about 50 to about 99% by weight of said composition. In other embodiments, the carrier, or mixture of carriers, is typically present in an amount of 75 to about 99% by weight of said composition.

The invention also provides methods of using the antimicrobial peptides and antimicrobial compositions of the invention to prevent, inhibit or terminate the growth of at least one microbe which may include, for example, bacteria, archaea, fungi, algae, protozoa, multicellular parasites, and viruses.

The methods of the invention include enteric administration. A typical dosage, for example is about 0.01 to about 100 mg/kg of peptide. Other embodiments of the methods of the invention include parenteral administration. A typical dosage is, for example about 0.01 to about 100 mg/kg of peptide. Topical administration is also provided. A typical dosage for topical administration may be, for instance, about 0.000001 to about 20% of peptide based on the weight of the composition. Inhalants are also provided wherein a typical dosage is, for example about 0.0001 to about 25 mg of peptide.

The invention also provides methods for treating an aqueous environment comprising at least one microbe with antimicrobial peptides or compositions thereof. In the methods of treating aqueous environments, peptides are typically present in an amount of about 0.001 to about 50% based on the weight percentage of the antimicrobial composition. Administration of peptides and carriers may be simultaneous, separate, continuous or intermittent.

The invention also provides methods for treating non-aqueous environments, comprising at least one microbe with antimicrobial peptides or compositions thereof. In the methods of treating non-aqueous environments, peptides are typically present in an amount of about 0.001 to about 75% based on the weight percentage of the antimicrobial composition. Administration of peptides and carriers may be simultaneous, separate, continuous or intermittent.

The invention also provides substrates coated with the antimicrobial compositions of the invention. Examples of substrates that may be coated with the antimicrobial compositions include, but are not limited to personal care products, healthcare products, household product, food preparation surfaces, food packaging surfaces, medical devices, wound dressings, surgical staples, membranes, shunts, surgical gloves, tissue patches, prosthetic devices, wound drainage tubes, blood collection and transfer devices, tracheotomy devices, intraocular lenses, laboratory devices, textile products, and painted surfaces.

These, as well as other aspects of the invention are set forth in greater detail below.

BRIEF DESCRIPTION OF DRAWINGS

The foregoing and other objects, features and advantages of the invention will be apparent from the following more particular description of the preferred embodiments, as illustrated in the accompanying drawings, and wherein:

FIG. 1 is a table demonstrating the minimum inhibitory concentration of acyl-modified peptides to inhibit the growth of at least 90% of Klebsiella pneumoniae and Pseudomonas aeruginosa. The peptides are attached to the Nα-amino group unless otherwise indicated.

FIG. 2 is a table demonstrating the minimum inhibitory concentration to inhibit at least 90% of Klebsiella pneumoniae and Pseudomonas aeruginosa. The peptides are N- and C-terminally modified with acyl chains of at least 4 carbon atoms; acyl groups are attached at the α-amino group on the N-terminal amino acid.

FIG. 3 is a table demonstrating minimum inhibitory concentration to inhibit at least 90% of the growth of clinically and industrially relevant organisms with peptides modified at the N- and C-terminus with acyl chains of 8 to 10 carbon atoms.

DETAILED DESCRIPTION OF THE INVENTION

The present invention is directed to peptides which are modified with at least one hydrocarbyl group and which possess antimicrobial activity. Peptides of the present invention may be used to combat microbes which include, but are not limited to, bacteria, archea, fungi (yeasts and molds), viruses, algae and parasites. These peptides may be used in various environments wherein antimicrobial treatment is desired, such as industrial and clinical settings. The peptides may be made in accordance with any appropriate method. The peptides of the present invention are characterized by specific properties as described below. These properties include, but are not limited to, hydrophobic, cationic and structural characteristics.

Further, peptides of the present invention may prevent, inhibit or terminate microbial growth via various mechanisms. Such mechanisms may be determined for peptides of the present invention using methods known in the art for structural prediction. The structural predictions may be useful in analyzing effects of peptides of the present invention on microbial structures including lipid bilayers. Preferably, structural prediction for peptides of the present invention may be performed using methods including computer-based modeling of peptides. Such computer-based models of peptides may include homology-based models or conformation-based models. For peptides of the present invention, computational prediction of antimicrobial activity may lead to determination of mechanisms of action which include, but are not limited to, disruption of the structure of the lipid bilayer via large scale movement of charged amino acid residues or disruption of the structure of the lipid bilayer via an increase in conformational dynamics of the peptide following insertion into the lipid bilayer.

As used herein, "peptide" refers to a single amino acid, or short span (e.g., 1–10) of amino acids.

The hydrocarbyl-modified peptides of the present invention possess activity toward microbes, which activity can be described as "antimicrobial." As used herein, the term "antimicrobial" is meant to include prevention, inhibition or termination of a microbe. "Prevention" can be considered to be the obstruction or hindrance of any potential microbial growth. "Inhibition" can be considered to be a reduction in microbial growth. This may occur via, but is not limited to, a microbiostatic mechanism such as interference in the synthesis of the cell wall or binding to ribosomal subunits to prevent production of microbial proteins. "Termination" can be considered to be actual killing of the microbes by the presence of the composition. This may occur via, but is not limited to, a microbiocidal mechanism such as a change in osmotic pressure leading to bursting of the cell or formation of leaky channels in the cell wall and membrane causing loss of cellular material.

As used herein, "microbes" is meant to include any organism comprised of the phylogenetic domains bacteria and archaea, as well as unicellular and filamentous fungi (such as yeasts and molds), unicellular and filamentous algae, unicellular and multicellular parasites, and viruses. The present invention is effective against bacteria including Gram-positive and Gram-negative cocci, Gram-positive and Gram-negative straight, curved and helical/vibroid and branched rods, sheathed bacteria, sulfur-oxidizing bacteria, sulfur or sulfate-reducing bacteria, spirochetes, actinomycetes and related genera, myxobacteria, mycoplasmas, rickettsias and chlamydias, cyanobacteria, archea, fungi, parasites, viruses and algae.

The Gram-positive and Gram-negative cocci include, but are not limited to, *Aerococcus, Enterococcus, Halococcus, Leuconostoc, Micrococcus, Mobiluncus, Moraxella catarrhalis, Neisseria* (including *N. gonorrheae* and *N. meningitidis*), *Pediococcus, Peptostreptococcus, Staphylococcus* species (including *S. aureus*, methicillin-resistant *S. aureus*, coagulase-negative *S. aureus*, and *S. saprophyticus*), *Streptococcus* species (including *S. pyogenes, S. agalactiae, S. bovis, S. pneumoniae, S. mutans, S. sanguis, S. equi, S. equinus, S. thermophilus, S. morbillorum, S. hansenii, S. pleomorphus,* and *S. parvulus*), and *Veillonella*.

The Gram-positive and Gram-negative straight, curved, helical/vibrioid and branched rods include, but are not limited to, *Acetobacter, Acinetobacter, Actinobacillus equuli, Aeromonas, Agrobacterium, Alcaligenes, Aquaspirillum, Arcanobacterium haemolyticum, Bacillus* species (including *B. cereus* and *B. anthracis*), *Bacteroides* species (including *B. fragilis*), *Bartonella, Bordetella* species (including *B. pertussis*), *Brochothrix, Brucella, Burkholderia cepacia, Calymmatobacterium granulomatis, Campylobacter* species (including *C. jejuni*), *Capnocytophaga, Caulobacter, Chromobacterium violaceum, Citrobacter, Clostridium* species (including *C. perfringens, C. tetani* and *C. difficile*), *Comamonas, Curtobacterium, Edwardsiella, Eikenella, Enterobacter, Erwinia, Erysipelothrix, Escherichia* species (including *E. coli*), *Flavobacterium* species (including *F. meninosepticum*), *Francisella* species (including *F. tularensis*), *Fusobacterium* (including *F. nucleatum*), *Gardnerella* species (including *G. vaginalis*), *Gluconobacter, Haemophilus* species (including *H. influenzae* and *H. ducreyi*), *Hafnia, Helicobacter* (including *H. pylori*), *Herpetosiphon, Klebsiella* species (including *K pneumoniae*), *Kluyvera, Lactobacillus, Legionella* species (including *L. pneumophila*), *Leptotrichia, Listeria* species (including *L. monocytogenes*), *Microbacterium, Morganella, Nitrobacter, Nitrosomonas, Pasteurella* species (including *P. multocida*), *Pectinatus, Porphyromonas gingivalis, Proteus* species (including *P. mirabilis*), *Providencia, Pseudomonas* species (including *P. aeruginosa, P. mallei, P. pseudomallei* and *P. solanacearum*), *Rahnella, Renibacterium salmoninarum, Salmonella, Serratia, Shigella, Spirillum, Streptobacillus* species (including *S. moniliformis*), *Vibrio* species (including *V. cholerae* and *V. vulnificus*), *Wolinella, Xanthobacter, Xenorhabdus, Yersinia* species (including *Y. pestis* and *Y. enterocolitica*), *Zanthomonas* and *Zymomonas*.

The sheathed bacteria include, but are not limited to, *Crenothrix, Leptothrix* and *Sphaerotilus*. The sulfur-oxidizing bacteria include, but are not limited to, *Beggiatoa, Gallionella, Sulfolobus, Thermothrix, Thiobacillus* species (including *T. ferroxidans*), *Thiomicrospira* and *Thiosphaera*. The sulfur or sulfate-reducing bacteria include, but are not limited to, *Desulfobacter, Desulfobulbus, Desulfococcus, Desulfomonas, Desulfosarcina, Desulfotomaculum, Desulfovibrio* and *Desulfuromonas*.

The spirochetes include, but are not limited to, *Treponema* species (including *T pallidum, T pertenue, T hyodysenteriae* and *T denticola*), *Borrelia* species (including *B. burgdorferi* and *B. recurrentis*), *Leptospira* and *Serpulina*.

The actinomycetes and related genera include, but are not limited to, *Acetobacterium, Actinomyces* species (including *A. israelii*), *Bifidobacterium, Brevibacterium, Corynebacterium* species (including *C. diphtheriae, C. insidiosum, C michiganese, C. rathayi, C. sepedonicum, C. nebraskense*), *Dermatophilus, Eubacterium, Mycobacterium* species (including *M. tuberculosis* and *M. leprae*), *Nocardia, Propionibacterium, Rhodococcus* and *Streptomyces*.

The myxobacteria include, but are not limited to, *Chondromyces, Cystobacter, Melittangium, Myxococcus, Nannocystis, Polyangium* and *Stigmatella*. The mycoplasmas include, but are not limited to, *Mycoplasma* species (including *M. pneumoniae*), Mycoplasma-like organisms of plants and invertebrates, *Spiroplasma* and *Ureaplasma* species (including *U. urealyticum*).

The rickettsias and chlamydias include, but are not limited to, *Aegyptianella, Anaplasma, Chlamydia* species (including *C. pneumoniae, C. trachomatis* and *C. psittaci*), *Cowdria, Coxiella, Ehrlichia, Eperythrozoon, Haemobartonella, Neorickettsia, Rickettsia* and *Rickettsiella*. The cyanobacteria include, but are not limited to, *Anabaena, Nostoc, Oscillatoria, Pleurocapsa, Prochloron* and *Synechococcus*.

The archea include, but are not limited to, all methanogens (*Methanobacterium, Methanobrevibacter, Methanococcoides, Methanococcus, Methanogenium, Methanolobus, Methanomicrobium, Methanoplanus, Methanosarcina, Methanospirillum, Methanothermus* and *Methanothrix*), and the genera *Acidianus, Archaeoglobus, Desulfurococcus, Haloarcula, Halobacterium, Halococcus, Haloferax, Natronobacterium, Natronococcus, Pyrococcus, Pyrodictium, Staphylothermus, Sulfolobus, Thermococcus, Thermophila, Thermoplasma* and *Thermoproteus*.

The present invention may also be used against fungi which include, but are not limited to, *Acremonium, Aspergillus, Blastomyces* species (including *B. dermatitidis*), *Candida* species (including *C. albicans*), *Ceratocystis, Chaetomium, Coccidioides* species (including *C. immitis*), *Cryptococcus neoformans, Epidermophyton, Fusarium* species (including *F. oxysporum*), *Gongronella, Histoplasma* species (including *H. capsulatum*), *Hormonea, Malassezia furfur, Microsporum, Mycosphaerella fijiensis, Paracoccidiodes brasiliensis, Penicillium, Pneumocystis carinii, Pythium, Rhizoctonia, Rhodotorula, Saccharomyces, Sporothrix schenckii, Torula, Trichoderma, Trichophyton* species (including *T. mentagrophytes* and *T rubrum*) and *Trichothecium*.

The present invention may be used against parasites which include, but are not limited to, *Acanthamoeba* species, *Ascaris lumbricoides, Babesia, Balamuthia, Balantidium, Blastocystis* species including *B. hominis, Chilomastix, Clonorchis sinensis, Cryptosporidium parvum, Cyclospora, Dientamoeba fragilis, Diphyllobothrium, Echinococcus, Endolimax, Entamoeba* species (including *E. histolytica*), *Enterobius* species (including *E. vermicularis*), *Giardia lamblia*, hookworms (including *Necator, Ancylostoma,* and *Unicinaria*), *Hymenolepsis, Iodamoeba, Isospora, Leishmania, Mansonella*, microsporidia, *Microsporidium, Naegleria fowleri, Onchocerca, Plasmodium* (including *P. falciparum, P. vivax, P. malariae,* and *P. ovale*), *Schistosoma* (including *S. haematobium* and *S. mansoni*), *Strongyloides* species (including *S. stercoralis*), tapeworms (including *Taenia* species), *Toxoplasma* (including *T. gondii*), *Trichinella* (including *T spiralis*), *Trichomonas vaginalis, Trichuris* species including *T. trichiura, Dirofilaria, Brugia, Wuchereria, Trypanosoma, Vorticella, Eimeria* species, *Hexamita* species and *Histomonas meleagidis*.

The present invention may also be used against viruses which include, but are not limited, to adenovirus, arborviruses (including hanta virus), astrovirus, coronavirus, cytomegalovirus, enteroviruses (including coxsackievirus A), Epstein-Barr virus, hepatitis A virus, hepatitis B virus, herpes viruses (including herpes simples virus or HSV), human immunodeficiency virus (HIV), human papilloma virus, human T-cell leukemia virus, influenza virus, mumps virus, Norwalk viruses, orbivirus, parainfluenzae viruses, parvovirus B19, poxviruses, Rabies virus, respiratory syncytial virus, rhinovirus, rotavirus, Rubella virus, varicella-zoster virus, vesicular stomatitis virus, cauliflower mosaic virus, cowpea mosaic virus, cowpox virus and rabbit myxomatis virus.

In addition, the present invention may be used against algae which include, but are not limited to, *Chlorella, Fragilaria, Gomphonema, Navicula, Nitzschia, Pfiesteria* (dinoflagellate), *Scenedesmus, Skeletoneona* and *Ulothrix.*

The hydrocarbyl-modified peptides of this invention are useful in the treatment of diseases caused by, but not limited to, bacteria, fungi, viruses and parasites in animals, plants, avian and aquatic organisms. The clinical diseases or infections caused by Gram-positive and/or Gram-negative bacteria, and treatable with the present invention include abscesses, bacteremia, contamination of peritoneal dialysis fluid, endocarditis, pneumonia, meningitis, osteomyelitis, cellulitis, pharyngitis, otitis media, sinusitis, scarlet fever, arthritis, urinary tract infection, laryngotracheitis, erysipeloid, gas gangrene, tetanus, typhoid fever, acute gastroenteritis, bronchitis, epiglottitis, plague, sepsis, chancroid, wound and burn infection, cholera, glanders, periodontitis, genital infections, empyema, granuloma inguinale, Legionnaire's disease, paratyphoid, bacillary dysentary, brucellosis, diphtheria, pertussis, botulism, toxic shock syndrome, mastitis, rheumatic fever, cystic fibrosis, eye infections, plaque, and dental caries. Other uses include swine erysipelas, peritonitis, abortion, encephalitis, anthrax, nocardiosis, pericarditis, mycetoma, peptic ulcer, melioidosis, Haverhill fever, tularemia, Moko disease, galls (such as crown, cane and leaf), hairy root, bacterial rot, bacterial blight, bacterial brown spot, bacterial wilt, bacterial fin rot, dropsy, columnaris disease, pasteurellosis, furunculosis, enteric redmouth disease, vibriosis of fish, fouling of medical devices.

Hydrocarbyl-modified peptides of the present invention may also be useful in treating diseases caused by spirochetes including syphilis, yaws, Lyme disease, Weil's disease, meningitis, leptospirosis, tick- and louse-borne relapsing fever, tick spirochetosis and canine, avian, rodent or lagomorph borreliosis. In addition, diseases caused by actinomycetes may be treatable by the present invention including tuberculosis, leprosy, cervicofacial lesions, abdominal lesions, thoracic lesions, pulmonary lesions and lesions of other organs, leafy gall and fish corynebacteriosis. Treatable rickettsial and chlamydial diseases or infections by the present invention include psittacosis, boutonneuse fever, ehrlichiosis, typhus fever, murine typhus, Brill's disease, Rocky Mountain spotted fever, Q fever, rickettsial pox, lymphogranuloma venereum, urethritis and trachoma. Treatable diseases or infections by mycoplasma include lethal yellowing.

Fungal infections treatable by the present invention include oral, cutaneous and vaginal thrush, cryptococcosis, superficial mycosis (including Athlete's foot), subcutaneous mycosis (including sporotrichosis), systemic mycosis (including histoplasmosis and coccidioidomycosis), Farmer's lung, aflatoxin disease, histoplasmosis, pneumonia, endocardititis, burn infections, mucormycosis, pityriasis versicolor, fungemia due to indwelling catheter infections, damping off, rot, panama disease, black leaf streak, anthracnose, apple scab, black knot, rust, canker, gray mold, blue mold, blight, powdery and downy mildew, wilt, damping off and leaf spot.

Viral infections treatable by the present invention include common colds, hemorrhagic fevers, mononucleosis, genital disease, keratoconjunctivitis, encephalitis, neonatal HSV, mucocutaneous HSV, chicken pox, retinitis, AIDS, influenza, pneumonia, bronchiolitis, genital papilloma, measles (including German measles), rabies, rubella, mumps, shingles, poliomyelitis, viral diarrhea, yellow fever, zoster, roseola, laryngotracheobronchitis, gastroenteritis, hepatitis (including hepatitis A and B), dengue fever, orf virus infection, molluscum contagiosum virus infection, fruit and vegetable mosaic viruses, tobacco ringspot virus, leaf curl virus, dropsy, cauliflower disease and necrotic viruses of fish.

Parasitic infections treatable by the present invention include trichinosis, schistosomiasis, encephalitis, keratitis, gastroenteritis, urogenital infections, toxoplasmosis, African sleeping sickness, malaria, amoebiasis, giardiasis, white spot disease, slimy skin disease, chilodonella, costia, hexamitiasis, velvet and coral fish disease.

Peptides of the present invention are also useful as infection or inflammation seeking agents or as T-cell activators.

The present invention is useful in a variety of environments including industrial, clinical, the household, and personal care. The hydrocarbyl-modified peptide compositions of the present invention for industrial, pharmaceutical, household and personal care use may comprise at least one active ingredient, of which the peptide of the present invention is an active ingredient acting alone, additively, or synergistically against the target microbe.

The hydrocarbyl-modified peptides of this invention may be delivered in a form suitable for use in environments including industry, pharmaceutics, household, and personal care. The peptides of the present invention are preferably soluble in water and may be applied or delivered with an acceptable carrier system. The composition may be applied or delivered with a suitable carrier system such that the active ingredient may be dispersed or dissolved in a stable manner so that the active ingredient, when it is administered directly or indirectly, is present in a form in which it is available in a particularly advantageous way.

Also, the separate components of the peptide compositions of the present invention may be preblended or each component may be added separately to the same environment according to a predetermined dosage for the purpose of achieving the desired concentration level of the treatment components and so long as the components eventually come into intimate admixture with each other. Further, the present invention may be administered or delivered on a continuous or intermittent basis.

The hydrocarbyl-modified peptides of the present invention, when present in a composition will preferably be present in an amount from about 0.000001% to about 100%, more preferably from about 0.001% to about 50%, and most preferably from about 0.01% to about 25%.

For compositions of the present invention comprising hydrocarbyl-modified peptides, when a carrier is present, the composition comprises preferably from about 1% to about 99%, more preferably from about 50% to about 99%, and most preferably from about 75% to about 99% by weight of at least one carrier.

The present invention and any suitable carrier may be prepared for delivery in forms including solution, microemulsion, suspension or aerosol. Generation of the aerosol or any other means of delivery of the present invention may be accomplished by any of the methods known in the art. For example, in the case of aerosol delivery, the antimicrobial composition is supplied in a finely divided form along with any suitable carrier with a propellant. Liquified propellants are typically gases at ambient conditions and are condensed under pressure. The propellant may be any acceptable and known in the art including propane and butane, or other lower alkanes, such as those of up to 5 carbons. The antimicrobial composition is held within a container with an appropriate propellant and valve, and maintained at elevated pressure until released by action of the valve.

The compositions may be prepared in a conventional form suitable for, but not limited to topical or local application such as an ointment, paste, gel, spray and liquid, by including stabilizers, penetrants and the carrier or diluent with peptide according to a known technique in the art. These preparations may be prepared in a conventional form suitable for enteral, parenteral, topical or inhalational applications.

The present invention may be used in compositions suitable for household use. For example, compositions of the present invention are also useful as an active antimicrobial ingredient in household products such as cleansers, detergents, disinfectants, dishwashing liquids, and soaps. The antimicrobial composition of the present invention may be delivered in an amount and form effective for the prevention, removal or termination of microbes.

The antimicrobial composition for household use may be defined as comprising at least one hydrocarbyl-modified peptide of the present application and at least one suitable carrier. Preferably, the composition comprises from about 0.00001% to about 50%, more preferably from about 0.0001% to about 25%, most preferably from about 0.0005% to about 10% by weight of hydrocarbyl-modified peptide based on the weight percentage of the total composition.

The present invention may further be used in hygiene compositions for personal care. For instance, compositions of the present invention are useful as an active ingredient in personal care products such as facial cleansers, astringents, body wash, shampoos, conditioners, cosmetics and other hygiene products. The hygiene composition may comprise any carrier or vehicle known in the art to obtain the desired form (such as solid, liquid, semisolid or aerosol) as long as the effects of the peptide of the present invention are not impaired. Methods of preparation of hygiene compositions are not described herein in detail, but are known in the art. For its discussion of such methods, THE CTFA COSMETIC INGREDIENT HANDBOOK, Second Edition, 1992, and pages 5–484 of A FORMULARY OF COSMETIC PREPARATIONS (Vol. 2, Chapters 7–16) are incorporated herein by reference.

The hygiene composition for use in personal care may be defined as comprising at least one hydrocarbyl-modified peptide of the present application and at least one suitable carrier. Preferably, the composition comprises from about 0.00001% to about 50%, more preferably from about 0.0001% to about 25%, most preferably from about 0.0005% to about 10% by weight of hydrocarbyl-modified peptide based on the weight percentage of the total composition.

The hydrocarbyl-modified peptides of the present invention may be used in industry. In the industrial setting, the presence of microbes can be problematic, as microbes are often responsible for industrial contamination and biofouling. Antimicrobial compositions for industrial applications comprise an effective amount of the hydrocarbyl-modified peptides of the present invention in an antimicrobial composition for industrial use with at least one acceptable carrier or vehicle known in the art to be useful in the treatment of such systems. Such carriers or vehicles may include diluents, deflocculating agents, penetrants, spreading agents, surfactants, suspending agents, wetting agents, stabilizing agents, compatability agents, sticking agents, waxes, oils, co-solvents, coupling agents, foams, antifoaming agents, natural or synthetic polymers, elastomers and synergists. Methods of preparation, delivery systems and carriers for such antimicrobial compositions are not described here in detail, but are known in the art. For its discussion of such methods, U.S. Pat. No. 5,939,086 is herein incorporated by reference. Furthermore, the preferred amount of antimicrobial composition to be used may vary according to the peptide and situation in which the composition is being applied.

The antimicrobial compositions of the present invention may be useful in nonaqueous environments. Such nonaqueous environments may include, but are not limited to, terrestrial environments, dry surfaces or semi-dry surfaces in which the antimicrobial composition is applied in a manner and amount suitable for the situation.

The antimicrobial compositions of the present invention may be used to form contact-killing coatings or layers on a variety of substrates including personal care products (such as toothbrushes, contact lens cases and dental equipment), healthcare products, household products, food preparation surfaces and packaging, and laboratory and scientific equipment. Further, other substrates include medical devices such as catheters, urological devices, blood collection and transfer devices, tracheotomy devices, intraocular lenses, wound dressings, sutures, surgical staples, membranes, shunts, gloves, tissue patches, prosthetic devices (e.g., heart valves) and wound drainage tubes. Still further, other substrates include textile products such as carpets and fabrics, paints and joint cement. A further use is as an antimicrobial soil fumigant.

The peptides may also be incorporated into polymers, such as polysaccharides (cellulose, cellulose derivatives, starch, pectins, alginate, chitin, guar, carrageenan), glycol polymers, polyesters, polyurethanes, polyacrylates, polyacrylonitrile, polyamides (e.g., nylons), polyolefins, polystyrenes, vinyl polymers, polypropylene, silks or biopolymers. The peptides may be conjugated to any polymeric material such as those with the following specified functionality: 1) carboxy acid, 2) amino group, 3) hydroxyl group and/or 4) haloalkyl group.

The antimicrobial composition for treatment of nonaqueous environments may be defined as comprising at least one peptide of the present invention and at least one suitable carrier. Preferably, the composition comprises from about 0.001% to about 75%, more preferably from about 0.01% to about 50%, most preferably from about 0.1% to about 25% by weight of hydrocarbyl-modified peptide based on the weight percentage of the total composition. The antimicrobial compositions of the present invention may be useful in aqueous environments. "Aqueous environments" as used herein, is meant to include any type of system containing water, including but not limited to, natural bodies of water such as lakes or ponds; artificial, recreational bodies of water such as swimming pools; and drinking reservoirs such as wells. The antimicrobial compositions of the present invention are useful in treating microbial growth in these aqueous environments and may be applied at or near the surface of water.

The antimicrobial composition for treatment of aqueous environments may be defined as comprising at least one peptide of the present application and at least one suitable carrier. Preferably, the composition comprises from about 0.001% to about 50%, more preferably from about 0.003% to about 15%, most preferably from about 0.01% to about 5% by weight of hydrocarbyl-modified peptide based on the weight percentage of the total composition.

The composition of the present invention may be administered for clinical use, in a therapeutically effective amount and composition, to beings infected with a microorganism discussed above. Beings treatable clinically include all land, air and water animals, and plants, but preferably mammals and most preferably humans. Alternatively, the composition may be administered prophylactically. The therapeutic and prophylactic dose for the present invention may vary according to several factors including the age, weight, and condition of the individual, route of administration and/or other drug interactions. The principles and factors for determining dosage are not discussed here in detail, but are known in the art and may be referenced in pages 1–83 of GOODMAN AND GILMAN'S THE PHARMACOLOGICAL BASIS OF THERAPEUTICS (8th Edition). The preferred doses for therapeutic and prophylactic treatment may vary and can be adjusted to suit the individual and situation.

The therapeutically and prophylactically effective amount is preferably from about 0.5 mg/kg to about 100 mg/kg, more preferably from about 1 mg/kg to about 20 mg/kg, and most preferably from about 2 mg/kg to about 10 mg/kg.

In addition to the foregoing, the present invention also provides a process for the production of a pharmaceutical composition. Such process comprises bringing at least one of the individual components described thereof into intimate admixture with a hydrocarbyl-modified peptide of the present invention, and when required, compounding the obtained composition in unit dosage form, for example filling said composition into gelatin, e.g., soft or hard gelatin, capsules. Methods of preparation of pharmaceutical compositions are not described here in detail, but are known in the art. For its discussion of such methods, pages 1435–1694 of REMINGTON'S PHARMACEUTICAL SCIENCES (Part 8) are incorporated herein by reference.

The pharmaceutical composition may be defined as comprising at least one hydrocarbyl-modified peptide of the present application and at least one suitable carrier. Preferably, the composition comprises from about 0.000001% to about 75%, more preferably from about 0.00001% to about 25%, most preferably from about 0.0001% to about 12% by weight of hydrocarbyl-modified peptide based on the weight percentage of the total composition.

The pharmaceutical composition may be administered for treatment of any land, air or water animal potentially having or having at least one microbial infection. Treatment of an animal with the present invention may also include prophylactic treatment. The mode of administration is such as to deliver a binding inhibiting effective amount of the pharmaceutical composition to the site of infection. For example, therapeutic delivery of the pharmaceutical composition may be achieved via enteral administration which includes oral, sublingual and rectal administration or via parenteral administration which includes intramuscular, intravenous and subcutaneous administration. Alternatively, therapeutic delivery of the pharmaceutical composition may also be achieved via other routes including topical and inhalational. Again, as discussed above, preferred dosage ranges will vary according to the individual and situation.

Enteral administration of the pharmaceutical composition is preferably administered at a dosage of from about 0.01 mg/kg to about 100 mg/kg, more preferably from about 2 mg/kg to about 50 mg/kg, and most preferably from about 5 mg/kg to about 30 mg/kg.

Parenteral administration of the pharmaceutical composition is preferably administered at a dosage from about 0.01 mg/kg to about 100 mg/kg, more preferably from about 1 mg/kg to about 30 mg/kg, and most preferably from about 5 mg/kg to about 25 mg/kg.

Topical administration of the pharmaceutical composition is preferably administered at a dosage from about 0.000001% to about 20%, more preferably from about 0.001% to about 15%, and most preferably from about 0.025% to about 10%.

Inhalational administration of the pharmaceutical composition is preferably administered at a dosage from about 0.0001 mg to about 25 mg, more preferably from about 0.01 mg to about 15 mg, and most preferably from about 0.1 mg to about 10 mg.

The peptides of this invention may be delivered in a pharmaceutically acceptable composition suitable for any of the routes of administration discussed above. "Pharmaceutically acceptable" is used herein to refer to those materials which are within the scope of sound medical judgement, suitable for use in contact with the tissue of humans and lower animals, avian and aquatic organisms without undue toxicity, irritation, allergic response and the like commensurate with a reasonable benefit/risk ratio, and effective for their intended use in the composition.

The pharmaceutical composition may include, but is not limited to, at least one acceptable carrier. The carrier is generally an inert bulk agent added to make the active ingredients easier to handle and can be solid, semisolid or liquid in the usual manner as well as understood in the art. Such a carrier may be a solvent, diluent or carrier comprising of waxes, cellulose derivatives, mineral oils, vegetable oils, petroleum derivatives, water, anhydrous lanolin, white petrolatum, liquid petrolatum, olive oil, ethanol and ethanol-polysorbate 80 solutions, propylene glycol-water solutions, and jojoba oils, methylcellulose or paraffin, beeswax, glyceryl stearate, PEG-2 stearate, propylene glycol stearate, glycol stearate, cetyl alcohol, stearyl alcohol, and any mixture thereof. Carriers used may include commercially available carriers or vehicles including Aquaphor ointment base (Beirsdorf Inc.,), Eucerin® creme/lotion (Beirsdorf), Acid Mantle® (Sandoz), Nutraderm® creme/lotion (Owen), Vehicle/N® or Vehicle/N® Mild (Neutrogena).

Pharmaceutical compositions of the invention may also include any delivery vehicle or device known in the art to enhance the transport of peptides across tissue and/or cell surfaces to reach the circulatory system and/or target site. Such delivery vehicles or devices may include liposomes or immunogenic liposomes, which may be adminstered in admixture with any carrier (discussed above) with regard to the intended route of administration, and standard pharmaceutical practice. Dosages of peptides associated with such delivery vehicles or devices will vary according to certain factors including the age, weight, and condition of the individual, as well as the pharmacokinetics and release characteristics of the peptide from the delivery vehicles or devices. Further, the ratio of peptide to liposome and carrier will depend on the chemical nature, solubility, trapping efficiency, and stability of the peptide, as well as the dosage anticipated. Maximal delivery of the peptide of the present invention may be accomplished by varying the lipid:peptide ratio as well as the type of peptide and liposome used.

The present invention also provides a process for the production of an antibiofouling composition for industrial use. Such process comprises bringing at least one of any industrially acceptable carrier known in the art into intimate admixture with a peptide of the present invention. The carrier may be any suitable carrier discussed above or known in the art.

The suitable antibiofouling compositions may be in any acceptable form for delivery of the composition to a site potentially having, or having at least one living microbe. The antibiofouling compositions may be delivered with at least one suitably selected carrier as hereinbefore discussed using standard formulations. The mode of delivery may be such as to have a binding inhibiting effective amount of the antibiofouling composition at a site potentially having, or having at least one living microbe. The antibiofouling compositions of the present invention are useful in treating microbial growth that contributes to biofouling, such as scum or slime formation, in these aqueous environments. Examples of industrial processes in which these compounds might be effective include cooling water systems, reverse osmosis membranes, pulp and paper systems, air washer systems and the food processing industry. The antibiofouling composition may be delivered in an amount and form effective for the prevention, removal or termination of microbes.

The antibiofouling composition of the present invention preferably comprises at least one hydrocarbyl-modified peptide from about 0.001% to about 50%, more preferably from about 0.003% to about 15%, most preferably from about 0.01% to about 5% by weight of hydrocarbyl-modified peptide based on the weight percentage of the total composition.

The amount of antibiofouling composition is preferably delivered in an amount of about 1 mg/l to about 1000 mg/l, more preferably from about 2 mg/l to about 500 mg/l, and most preferably from about 20 mg/l to about 140 mg/l.

The peptides of the present invention may be delivered at a minimum inhibitory concentration. The "minimum inhibitory concentration" (MIC) is used herein to refer to the lowest concentration of the peptides of the present invention required to inhibit greater than or equal to 90% microbial growth. The MIC for the peptides of the present invention is preferably less than or equal to 100 µg/ml, more preferably less than or equal to 50 µg/ml, and most preferably less than or equal to 10 µg/ml.

The peptides of the present invention are modified at the N- and/or C-terminus. "Modifications" as used herein include modifications at the N-terminus and/or C-terminus or modification of any position on at least one amino acid residue. The modified peptides are represented by Formulae I and II:

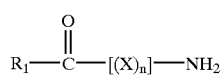

Formula I

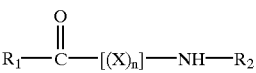

Formula II wherein:
X represents any of the natural or non-natural, modified or unmodified amino acids except glutamate (Glu) or aspartate (Asp);
n=1 to 10;
$R_1$ is $C_1$–$C_{20}$ alkyl; $C_3$–$C_6$ cycloalkyl; $C_4$–$C_{20}$ alkenyl; $C_4$–$C_{20}$ alkynyl; $C_1$–$C_{20}$ haloalkyl; $C_3$–$C_{20}$ haloalk-enyl; $C_3$–$C_{20}$ haloalkynyl; $C_2$–$C_{20}$ alkoxyalkyl; $C_2$–$C_{20}$ alkylthioalkyl; $C_2$–$C_{20}$ alkylsulfinylalkyl; $C_2$–$C_{20}$ alkylsulfonylalkyl; $C_5$–$C_{20}$ cycloalkylalkyl; $C_4$–$C_{20}$ alkenyloxyalkyl; $C_4$–$C_{20}$ alkynyloxyalkyl; $C_4$–$C_{20}$ (cycloalkyl)oxyalkyl; $C_4$–$C_{20}$ alkenylthioalkyl; $C_4$–$C_{20}$ alkynylthioalkyl; $C_6$–$C_{20}$ (cycloalkyl)thioalkyl; $C_2$–$C_{20}$ haloalkoxyalkyl; $C_4$–$C_{20}$ haloalkenyloxyalkyl; $C_4$–$C_{20}$ haloalkynyloxyalkyl; $C_4$–$C_{20}$ alkoxylalkenyl; $C_4$–$C_{20}$ alkoxyalkynyl; $C_4$–$C_{20}$ alkylthioalkenyl; $C_4$–$C_{20}$ alkylthioalkynyl; $C_4$–$C_{20}$ trialkylsilylalkyl; $C_1$–$C_{20}$ alkyl substituted with $NR_3R_4$, nitro, cyano, or phenyl optionally substituted with $R_5$, $R_6$, and $R_7$; $C_1$–$C_{20}$ alkoxy; $C_1$–$C_{20}$ haloalkoxy; $C_1$–$C_{20}$ alkylthio; $C_1$–$C_{20}$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;

$R_2$ is $C_1$–$C_{20}$ alkyl; $C_3$–$C_6$ cycloalkyl; $C_4$–$C_{20}$ alkenyl; $C_4$–$C_{20}$ alkynyl; $C_1$–$C_{20}$ haloaokyl; $C_3$–$C_{20}$ haloalk-enyl; $C_3$–$C_{20}$ haloalkynyl; $C_2$–$C_{20}$ alkoxyalkyl; $C_2$–$C_{20}$ alkylthioalkyl; $C_2$–$C_{20}$ alkylsulfinylalkyl; $C_2$–$C_{20}$ alkylsulfonylalkyl; $C_5$–$C_{20}$ cycloalkylalkyl; $C_4$–$C_{20}$ alkenyloxyalkyl; $C_4$–$C_{20}$ alkynyloxyalkyl; $C_4$–$C_{20}$ (cycloalkyl)oxyalkyl; $C_4$–$C_{20}$ alkenylthioalkyl; $C_4$–$C_{20}$ alkynylthioalkyl; $C_6$–$C_{20}$ (cycloalkyl)thioalkyl; $C_2$–$C_{20}$ haloalkoxyalkyl; $C_4$–$C_{20}$ haloalkenyloxyalkyl; $C_4$–$C_{20}$ haloalkynyloxyalkyl; $C_4$–$C_{20}$ alkoxylalkenyl; $C_4$–$C_{20}$ alkoxyalkynyl; $C_4$–$C_{20}$ alkylthioalkenyl; $C_4$–$C_{20}$ alkylthioalkynyl; $C_4$–$C_{20}$ trialkylsilylalkyl; $C_1$–$C_{20}$ alkyl substituted with $NR_3R_4$, nitro, cyano, or phenyl optionally substituted with $R_5$, $R_6$, and $R_7$; $C_1$–$C_{20}$ alkoxy; $C_1$–$C_{20}$ haloalkoxy; $C_1$–$C_{20}$ alkylthio; $C_1$–$C_{20}$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;

$R_3$ is independently hydrogen; $C_1$–$C_4$ alkyl; or phenyl optionally substituted with at least one $R_8$;

$R_4$ is independently hydrogen; $C_1$–$C_8$ alkyl; or phenyl optionally substituted with at least one $R_8$;

$R_5$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R_8$; cyano; nitro; $C_1$–$C_6$ haloalkoxy; $C_1$–$C_6$ haloalkythio; $C_2$–$C_6$ alkenyl; $C_2$–$C_6$ haloalkenyl; acetyl; $CO_2CH_3$; or $N(C_1$–$C_2$ alkyl$)_2$;

$R_6$ is independently methyl; ethyl; methoxy; methylthio; halogen; or trifluoromethyl;

$R_7$ is independently halogen; and $R_8$ is independently halogen; $C_1$–$C_4$ alkyl; $C_1$–$C_4$ alkoxy; $C_1$–$C_4$ haloalkyl; nitro; or cyano.

In some embodiments, when said peptide is 2–3 amino acids, at least two of the amino acids are cationic amino acids; the net charge of said peptide at neutral pH is at least +1;

$R_1$ is $C_1$–$C_9$ alkyl; $C_3$–$C_6$ cycloalkyl; $C_4$–$C_9$ alkenyl; $C_4$–$C_9$ alkynyl; $C_1$–$C_9$ haloalkyl; $C_3$–$C_9$ haloalkenyl; $C_3$–$C_9$ haloalkynyl; $C_2$–$C_9$ alkoxyalkyl; $C_2$–$C_9$ alkylthioalkyl; $C_2$–$C_9$ alkylsulfinylalkyl; $C_2$–$C_9$ alkylsulfonylalkyl; $C_5$–$C_9$ cycloalkylalkyl; $C_4$–$C_9$ alkenyloxyalkyl; $C_4$–$C_9$ alkynyloxyalkyl; $C_4$–$C_9$ (cycloalkyl)oxyalkyl; $C_4$–$C_9$ alkenylthioalkyl; $C_4$–$C_9$ alkynylthioalkyl; $C_6$–$C_9$ (cycloalkyl)thioalkyl; $C_2$–$C_9$ haloalkoxyalkyl; $C_4$–$C_9$ haloalkenyloxyalkyl; $C_4$–$C_9$ haloalkynyloxyalkyl; $C_4$–$C_9$ alkoxylalkenyl; $C_4$–$C_9$ alkoxyalkynyl; $C_4$–$C_9$ alkylthioalkenyl; $C_4$–$C_9$ alkylthioalkynyl; $C_4$–$C_9$ trialkylsilylalkyl; $C_1$–$C_9$ alkyl substituted with $NR_3R_4$, nitro, cyano, or phenyl optionally substituted with $R_5$, $R_6$, and $R_7$; $C_1$–$C_9$ alkoxy; $C_1$–$C_9$ haloalkoxy; $C_1$–$C_9$ alkylthio; $C_1$–$C_9$ haloalkylthio; $NR_3R_4$; or phenyl, benzyl, pyridyl, furanyl, thienyl, naphthyl, pyrimidinyl, benzofuranyl, benzothienyl, or quinolinyl each optionally substituted with $R_5$, $R_6$ or $R_7$;

$R_3$ is independently hydrogen; $C_1$–$C_4$ alkyl; or phenyl optionally substituted with at least one $R_8$;

$R_4$ is independently hydrogen; $C_1$–$C_8$ alkyl; or phenyl optionally substituted with at least one $R_8$;

$R_5$ is independently $C_1$–$C_6$ alkyl; $C_1$–$C_6$ alkoxy; $C_1$–$C_6$ haloalkyl; halogen; $C_2$–$C_8$ alkynyl; $C_1$–$C_6$ thioalkyl; phenyl or phenoxy each optionally substituted with at least one $R_8$; cyano; nitro; $C_1$–$C_6$ haloalkoxy; $C_1$–$C_6$ haloalkythio; $C_2$–$C_6$ alkenyl; $C_2$–$C_6$ haloalkenyl; acetyl; $CO_2CH_3$; or $N(C_1$–$C_2$ alkyl$)_2$;

$R_6$ is independently methyl; ethyl; methoxy; methylthio; halogen; or trifluoromethyl;

$R_7$ is independently halogen; and $R_8$ is independently halogen; $C_1$–$C_4$ alkyl; $C_1$–$C_4$ alkoxy; $C_1$–$C_4$ haloalkyl; nitro; or cyano.

As used herein, "hydrocarbyl" is defined by $R_1$ and $R_2$.

In the above recitations, the term "alkyl", used either alone or in compound words such as "alkylthio," "haloalkyl," or "alkylthioalkyl" denotes straight-chain or branched alkyl; e.g., methyl, ethyl, n-propyl, i-propyl, or the different butyl, pentyl, hexyl, etc. isomers.

"Cycloalkyl" denotes cyclopropyl, cyclobutyl, cyclopentyl, and cyclohexyl. The term "cycloalkyloxyalkyl" denotes the cycloalkyl groups linked through an oxygen atom to an alkyl chain. Examples include cyclopentyloxymethyl and cyclohexyloxybutyl. The term "cycloalkylthioalkyl" are the cycloalkyl groups linked through a sulfur atom to an alkyl chain; e.g., cyclopropylthiopentyl. "Cycloalkylalkyl" denotes a cycloalkyl ring attached to a branched or straight-chain alkyl; e.g. cyclopropylmethyl and cyclohexylbutyl.

"Cycloalkylalkyl" denotes a cycloalkyl ring attached to a branched or straight-chain alkyl; e.g. cyclopropylmethyl and cyclohexylbutyl.

"Alkenyl" denotes straight chain or branched alkenes; e.g., 1-propenyl, 2-propenyl, 3-propenyl and the different butenyl, pentenyl, hexenyl, etc. isomers. Alkenyl also denotes polyenes such as 1,3-hexadiene and 2,4,6-heptatriene.

"Alkynyl" denotes straight chain or branched alkynes; e.g., ethynyl, 1-propynyl, 3-propynyl and the different butynyl, pentynyl, hexynyl, etc. isomers. "Alkynyl" can also denote moieties comprised of multiple triple bonds; e.g., 2,7-octadiyne and 2,5,8-decatriyne.

"Alkoxy" denotes methoxy, ethoxy, n-propyloxy, isopropyloxy and the different butoxy, pentoxy, hexyloxy, etc. isomers. "Alkoxyalkenyl" and "alkoxyalkynyl" denoted groups in which the alkoxy group is bonded through the oxygen atom to an alkenyl or alkynyl group, respectively. Examples include $CH_3OCH_2CH\equiv CH$ and $(CH_3)_2CHOCH_2C\equiv CCH_2$. The corresponding sulfur derivatives are denoted "alkylthioalkenyl" and "alkylthioalkynyl." Examples of the former include $CH_3SCH_2CH=CH$ and $CH_3CH_2SCH_2(CH_3)CH=CHCH_2$, and an example of the latter is $CH_3CH_2CH_2SCH_2C\equiv C$.

"Alkenyloxy" denotes straight chain or branched alkenyloxy moieties. Examples of alkenyloxy include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkenylthio" denotes the similar groups wherein the oxygen atom is replaced with a sulfur atom; e.g., $H_2C=CHCH_2S$ and $(CH_3)CH=C(CH_3)CH_2S$. The term "alkenyloxyalkyl" denotes groups in which the alkenyloxy moiety is attached to an alkyl group. Examples include $H_2C=CHCH_2OCH_2CH_2$, $H_2C=CHCH_2OCH(CH_3)CH_2$, etc. "Alkenylthioalkyl" denotes the alkenylthio moieties bonded to an alkyl group. Examples include $H_2C=CHCH_2SCH(CH_3)CH(CH_3)$ and $(CH_3)CH=C(CH_3)CH_2SCH_2$.

"Alkynyloxy" denotes straight or branched alkynyloxy moieties. Examples include $HC\equiv CCH_2O$, $CH_3C\equiv CCH_2O$ and $CH_3C\equiv CCH_2CH_2O$. "Alkynyloxyalkyl" denotes alkynyloxy moieties bonded to alkyl groups; e.g., $CH_3C\equiv CCH_2OCH_2CH_2$ and $HC\equiv CCH_2OCH(CH_3)CH_2$. "Alkynylthioalkyl" denotes alkynylthio moieties bonded to alkyl groups. Example include $CH_3C\equiv CCH_2SCH_2CH_2$ and $CH_3C\equiv CCH_2CH_2SCH(CH_3)CH_2$.

"Alkylthio" denotes methylthio, ethylthio, and the different propylthio, butylthio, pentylthio and hexylthio isomers. "Alkylthioalkyl" denotes alkylthio groups attached to an alkyl chain; e.g., $CH_3CH_2SCH_2CH(CH_3)$ and $(CH_3)_2CHSCH_2$.

"Alkylsulfinyl" denotes both enantiomers of an alkylsulfinyl group. For example, $CH_3S(O)$, $CH_3CH_2S(O)$, $CH_3CH_2CH_2S(O)$, $(CH_3)_2CHS(O)$ and the different butylsulfinyl, pentylsulfinyl and hexylsufinyl isomers. "Alkylsulfinylalkyl" denotes alkylsulfinyl groups attached to an alkyl chain; e.g., $CH_3CH_2S(O)CH_2CH(CH_3)$ and $(CH_3)_2CHS(O)CH_2$.

Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylsulfonylalkyl" denotes alkylsulfonyl groups attached to an alkyl chain; e.g., $CH_3CH_2S(O)_2CH_2CH(CH3)$ and $(CH_3)_2CHS(O)_2CH_2$.

The term "halogen", either alone or in compound words such as "haloalkyl", denotes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CF_2$. Examples of "haloalkenyl" include $(Cl)_2C=CHCH_2$ and $CF_3CH_2CH=CHCH_2$. "Haloalkenyloxyalkyl" denotes haloalkenyl groups bonded to oxygen and in turn bonded to alkyl groups. Examples include $CF_3CH_2CH=CHCH_2OCH_2$ and $(Cl)_2C=CHCH_2OCH_2CH_2$. Examples of "haloalkynyl" include $HC\equiv CCHCl$, $CF_3C\equiv C$, $CCl_3C\equiv C$ and $FCH_2C\equiv CCH_2$. "Haloalkynyloxyalkyl" denotes haloalkynyl groups bonded through an oxygen atom to an alkyl moiety. Examples include $CF_3C\equiv CCH_2OCH_2CH_2$, $ClCH_2C\equiv CCH_2CH_2OCH(CH_3)$, etc. Examples of "haloalkoxy" include $CF_3O$, $CCl_3CH_2O$, $CF_2HCH_2CH_2O$ and $CF_3CH_2O$. "Haloalkoxyalkyl" denotes haloalkoxy groups bonded to straight-chain or branched alkyl groups; e.g., $CF_2HCH_2CH_2OCH_2CH_2$, $CCl_3CH_2OCH(CH_3)$ and $CF_3OCH_2$.

"Trialkylsilyl" designates a group with three alkyl groups bonded to silicon; e.g., $(CH_3)_3Si$ and $t$-$Bu(CH_3)_2Si$. "Trialkylsilylalkyl" denotes trialkylsilyl groups bonded to another straight-chain or branched alkyl group. Examples include $(CH_3)_3SiCH_2$ and $t$-$Bu(CH_3)_2SiCH_2CH(CH_3)CH_2$.

The total number of carbon atoms in a substituent group is indicated by the "$C_i$–$C_j$" prefix where i and j are numbers from 1 to 10. For example, $C_1$–$C_3$ alkylsulfonyl designates methylsulfonyl through propylsulfonyl; $C_2$ alkoxyalkoxy designates $CH_3OCH_2O$; $C_3$ alkoxyalkoxy designates, for example, $CH_3OCH_2CH_2O$ or $CH_3CH_2OCH_2O$; and $C_4$ alkoxyalkoxy designates the various isomers of an alkoxy group substituted with a second alkoxy group containing a total of 4 carbon atoms, examples including $CH_3CH_2CH_2OCH_2O$, and $CH_3CH_2OCH_2CH_2O$. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

Amino acid chains are from N-terminus to C-terminus. Furthermore, in the formulae, the $R_1(C=O)$— group is bound to the alpha nitrogen of the N-terminal amino acid of the peptide. The —$NH_2$ group (Formula I) or the —NH—$R_2$ group (Formula II) is bound to the carbon of the alpha carboxyl group of the C-terminal amino acid.

Preferably $R_1$ comprises from about 5 to about 15 carbon atoms, and more preferably comprises from about 6 to about 11 carbon atoms. Preferably $R_1$ comprises an alkyl group having from about 1 to about 20 carbon atoms. Preferably the alkyl group comprises from about 5 to about 15 carbon atoms, and more preferably comprises from about 6 to about 11 carbon atoms.

Preferably $R_2$ comprises 5 to 15 carbon atoms, and more preferably from about 6 to about 11 carbon atoms. Preferably, $R_2$ comprises hydrogen, or $R_2$ comprises an alkyl group. When $R_2$ is an alkyl group, preferably $R_2$ comprises from about 5 to about 15 carbon atoms, and more preferably from about 6 to about 11 carbon atoms.

Peptides of the present invention may comprise residues from any of the naturally-occurring amino acids, or from non-naturally-occurring amino acids. These naturally-occurring and non-naturally-occurring amino acids may be in the D or L configuration. The terms D and L are used herein as they are known to be used in the art. Peptides of the invention include single amino acids and short spans (e.g., 1–10) of amino acids. In addition, modified peptides of the present invention may also comprise a monomer or dimer.

The standard single letter and three letter codes for amino acids are used herein and are as follows:

| | | |
|---|---|---|
| A (Ala) Alanine | C (Cys) Cysteine | D (Asp) Aspartic acid |
| E (Glu) Glutamic acid | F (Phe) Phenylalanine | G (Gly) Glycine |
| H (His) Histidine | I (Ile) Isoleucine | K (Lys) Lysine |
| L (Leu) Leucine | M (Met) Methionine | N (Asn) Asp aragine |
| P (Pro) Proline | Q (Gln) Glutamine | R (Arg) Arginine |
| S (Ser) Serine | T (Thr) Threonine | V (Val) Valine |
| W (Trp) Tryptophan | Y (Tyr) Tyrosine | |

The amino acids of the peptides of the present invention may also be modified. For example, amino groups may be acylated, alkylated or arylated. Benzyl groups may be halogenated, nitrosylated, alkylated, sulfonated or acylated. These modifications are meant to be illustrative and not comprehensive of the types of modifications possible. Modification of the amino acids would likely add to the cost of synthesis and therefore is not preferred.

The present invention comprises peptides with antimicrobial activity. Peptides of the present invention are peptides having from about 1 to about 10, preferably from about 1 to about 6, and most preferably from about 1 to about 4 amino acid residues.

The peptides of the present invention comprise at least one amino acid residue, whereby the composition can be expressed by $X_n$ where n=1 to 10. Thus, peptides according to the present invention can be represented by:

$X_1$
$X_1X_2$
$X_1X_2X_3$
$X_1X_2X_3X_4$
$X_1X_2X_3X_4X_5$
$X_1X_2X_3X_4X_5X_6$
$X_1X_2X_3X_4X_5X_6X_7$
$X_1X_2X_3X_4X_5X_6X_7X_8$
$X_1X_2X_3X_4X_5X_6X_7X_8X_9$
$X_1X_2X_3X_4X_5X_6X_7X_8X_9X_{10}$

Most preferred, however, are shorter chains of amino acids. This is a preference based on cost. Longer peptides may perform as well as, or even better than, shorter peptides (with fewer amino acid residues), but are less preferred for economic reasons.

The peptides according to the present invention include cationic and uncharged amino acids. For peptides of one to three amino acids (n=1–3), one amino acid in positions $X_1$, $X_2$ or $X_3$ is preferably a cationic amino acid, such that the net charge of the peptide at neutral pH is at least +1. The net positive charge for the peptides of the present invention is determined by summing the charges of each of the amino acids. The cationic amino acids may include arginine (Arg), lysine (Lys), ornithine (Orn) or histidine (His). Preferably, the cationic amino acids are Arg, Lys or Orn; the most preferred amino acid is arginine. The remaining amino acids include all amino acids, preferably not negatively charged amino acids such as Glutamate (Glu) or Aspartate (Asp). The remaining amino acids may include phenylalanine (Phe), tryptophan (Trp), tyrosine (Tyr), alanine (Ala), glycine (Gly), isoleucine (Ile), leucine (Leu), proline (Pro), valine (Val), cysteine (Cys), methionine (Met), serine (Ser), threonine (Thr), asparagine (Asn), glutamine (Gln), 2-naphthylalanine (Nal), Arg, Lys, Orn or His.

For reasons facilitating manufacture, peptides of the present invention comprise preferably one or two, or possibly three amino acids. However, longer peptides may demonstrate increased efficacy. Thus, for peptides of four or five amino acids (n=4–5), at least two of the amino acids in positions $X_1$ through $X_5$ are preferably cationic amino acids such as Arg, Lys or Orn; Arg is the preferred amino acid. The remaining amino acids may comprise any amino acid, preferably not Glu or Asp; the net charge of the peptide at neutral pH is preferably at least +2.

For peptides of six to eight amino acids (n=6–8), it is prefered that at least three of the amino acids in positions $X_1$ through $X_8$ are cationic amino acids such as Arg, Lys or Orn; Arg is the preferred amino acid. The remaining amino acids may comprise any amino acid, preferably not Glu or Asp; the net charge of the peptide at neutral pH is preferably at least +3. When the peptide is an N-terminally hydrocarbyl-modified hexapeptide with a C-terminal amido group, the peptides of the invention are not Phe-Arg-Trp-Trp-His-Xaa (SEQ ID NO:24), Arg-Arg-Trp-Trp-Met-Xaa (SEQ ID NO:25), Arg-Arg-Trp-Trp-Cys-Xaa (SEQ ID NO:26), or Arg-Arg-Trp-Trp-Arg-Xaa (SEQ ID NO:27), where "Xaa" refers to any amino acid. When the peptide is an N-terminally hydrocarbyl-modified heptapeptide with a C-terminal amido group, the peptides of the invention are not Arg-Arg-Trp-Trp-Cys-Xaa-Xaa (SEQ ID NO:28), where "Xaa" refers to any amino acid.

For peptides of nine to ten amino acids (n=9–10), it is prefered that at least four of the amino acids in positions $X_1$ through $X_{10}$ are cationic amino acids such as Arg, Lys or Orn; Arg is the preferred amino acid. The remaining amino acids may comprise any amino acid, preferably not Glu or Asp; the net charge of the peptide at neutral pH is preferably at least +4.

Further, for peptides which are modified with a single hydrocarbyl group (Formula I), when n=2, it is prefered that one amino acid is a cationic amino acid such as Arg, Lys or Orn. The remaining amino acid may be any amino acid, preferably not Glu or Asp; the amino acid may include Phe, Trp, Tyr, Ala, Gly, Ile, Leu, Pro, Val, Cys, Met, Ser, Thr, Asn, Gln, Nal, Arg, Lys, Orn or His. The most preferred amino acid is Trp.

In addition, for peptides of three amino acids that are modified with a single hydrocarbyl group, it is prefered that at least one amino acid in positions $X_1$, $X_2$ or $X_3$ is a cationic amino acid such as Arg, Lys, or Orn. Further, it is prefered that at least one amino acid in positions $X_1$, $X_2$ or $X_3$ is Trp. The remaining amino acid may include any amino acid, preferably not Glu or Asp, however, the net charge of the peptide at neutral pH is preferably at least +1.

In addition, for peptides of four or five amino acids which are modified with a single hydrocarbyl group, it is preferable that at least two amino acids in positions $X_1$ through $X_5$ are cationic amino acids such as Arg, Lys, or Orn. Further, it is prefered that at least one amino acid in positions $X_1$ through $X_5$ is Trp. The remaining amino acid may include any amino acid, preferably not Glu or Asp, however, the net charge of the peptide at neutral pH is preferably at least +2.

In addition, for peptides of six to eight amino acids which are modified with a single hydrocarbyl group, it is prefered that at least three amino acids in positions $X_1$ through $X_8$ are cationic amino acids such as Arg, Lys, or Orn. Further, it is prefered that least two amino acids in positions $X_1$ through $X_8$ are Trp. The remaining amino acids may include any amino acid, preferably not Glu or Asp, however, the net charge of the peptide at neutral pH is preferably at least +3.

In addition, for peptides of nine to ten amino acids that are modified with a single hydrocarbyl group, it is prefered that at least four amino acids in positions $X_1$ through $X_{10}$ are cationic amino acids such as Arg, Lys, or Orn. Further, it is prefered that at least three amino acids in positions $X_1$ through $X_{10}$ are Trp. The remaining amino acids may include any amino acid, preferably not Glu or Asp, however, the net charge of the peptide at neutral pH is preferably at least +4.

Examples of less preferred peptides, except for those peptides modified with two hydrocarbyl groups, comprise peptides having at least 5 to 10 amino acid residues. This preference is based upon economical factors in the manufacturing process.

Preferred peptides of the present invention (except for those modified with two hydrocarbyl groups) include:

| | |
|---|---|
| Arg-Phe-Arg | Lys-Phe-Arg |
| Lys-Phe-Lys | Arg-Phe-Lys |
| Orn-Phe-Arg | Orn-Phe-Orn |
| Arg-Phe-Orn | |
| Arg-Trp-Phe-Arg (SEQ ID NO:1) | Arg-Trp-Arg-Phe (SEQ ID NO:2) |
| Arg-Trp-Trp-Arg (SEQ ID NO:3) | Arg-Arg-Trp-Phe (SEQ ID NO:4) |
| Arg-Trp-Arg-Trp (SEQ ID NO:5) | Arg-Phe-Arg-Trp (SEQ ID NO:6) |
| Arg-Arg-Phe-Trp (SEQ ID NO:7) | Arg-Trp-Ala-Arg (SEQ ID NO:8) |
| Arg-Trp-Tyr-Arg (SEQ ID NO:9) | Arg-Trp-Ile-Arg (SEQ ID NO:10) |
| Arg-Trp-Leu-Arg (SEQ ID NO:11) | Arg-Trp-Pro-Arg (SEQ ID NO:12) |
| Arg-Trp-Val-Arg (SEQ ID NO:13) | Arg-Trp-Cys-Arg (SEQ ID NO:14) |
| Arg-Trp-Met-Arg (SEQ ID NO:15) | Arg-Trp-Ser-Arg (SEQ ID NO:16) |
| Arg-Trp-Thr-Arg (SEQ ID NO:17) | Arg-Trp-Asn-Arg (SEQ ID NO:18) |
| Arg-Trp-Gln-Arg (SEQ ID NO:19) | Arg-Trp-Nal-Arg (SEQ ID NO:20) |

-continued

| | |
|---|---|
| Arg-Trp-His-Arg (SEQ ID NO:21) | Arg-Trp-Lys-Arg (SEQ ID NO:22) |
| Arg-Trp-Gly-Arg (SEQ ID NO:23) | |

The most preferred peptides of the present invention (except those modified with two hydrocarbyl groups) are short peptides including:

| | |
|---|---|
| Arg-Trp | Lys-Trp |
| Orn-Trp | Arg-Trp-Phe |
| Lys-Trp-Phe | Orn-Trp-Phe |
| Arg-Trp-Cys | Lys-Trp-Cys |
| Orn-Trp-Cys | Arg-Phe-Trp |
| Lys-Phe-Trp | Orn-Phe-Trp |
| Arg-Arg-Trp | Lys-Lys-Trp |
| Lys-Arg-Trp | Arg-Lys-Trp |
| Orn-Orn-Trp | Orn-Arg-Trp |
| Arg-Orn-Trp | Arg-Trp-Arg |
| Lys-Trp-Arg | Arg-Trp-Lys |
| Lys-Trp-Lys | Orn-Trp-Arg |
| Arg-Trp-Orn | Orn-Trp-Orn |

Still further, for peptides modified with two hydrocarbyl groups, when n=1, the amino acid in position $X_1$ is preferably a cationic amino acid such as Arg, Lys or Orn. Arginine is the preferred amino acid.

In addition, for peptides which are two amino acids in length and which are modified with two hydrocarbyl groups, it is prefered that at least one amino acid in positions $X_1$ and $X_2$ is a cationic amino acid such as Arg, Lys or Orn. The remaining amino acid may include any amino acid, preferably not Glu or Asp; the amino acid may include Phe, Trp, Tyr, Ala, Gly, Ile, Leu, Pro, Val, Cys, Met, Ser, Thr, Asn, Gln, Nal, Arg, Lys, Orn or His. The net positive charge of the peptide at neutral pH is preferably at least +1.

In addition, for peptides which are three amino acids in length and which are modified with two hydrocarbyl groups, it is prefered that at least one amino acid in positions $X_1$, $X_2$ or $X_3$ is a cationic amino acid such as Arg, Lys or Orn. The remaining amino acids may include any amino acid, preferably not Glu or Asp; the amino acid may include Phe, Trp, Tyr, Ala, Gly, Ile, Leu, Pro, Val, Cys, Met, Ser, Thr, Asn, Gln, Nal, Arg, Lys, Orn or His. Preferably two of the amino acids are cationic amino acids, preferably the cationic amino acids are Arg. The net positive charge of the peptide at neutral pH is preferably at least +1.

In addition, for peptides which are four amino acids in length and which are modified with two hydrocarbyl groups, it is prefered that at least two amino acids in positions $X_1$, $X_2$, $X_3$ or $X_4$ are cationic amino acids such as Arg, Lys or Orn. The remaining amino acids may include any amino acid, preferably not Glu or Asp; the amino acids may include Phe, Trp, Tyr, Ala, Gly, Ile, Leu, Pro, Val, Cys, Met, Ser, Thr, Asn, Gln, Nal, Arg, Lys, Orn or His. The net positive charge of the peptide at neutral pH is preferably at least +2.

In addition, for peptides which are five to seven amino acids in length and which are modified with two hydrocarbyl groups, it is prefered that at least three amino acids in positions $X_1$ through $X_7$ are cationic amino acids such as Arg, Lys or Orn. The remaining amino acids may include any amino acid, preferably not Glu or Asp; the amino acids may include Phe, Trp, Tyr, Ala, Gly, Ile, Leu, Pro, Val, Cys, Met, Ser, Thr, Asn, Gln, Nal, Arg, Lys, Orn or His. The net positive charge of the peptide at neutral pH is preferably at least +3.

In addition, for peptides which are eight to ten amino acids in length and which are modified with two hydrocarbyl groups, it is preferred that at least four amino acids in positions $X_1$ through $X_{10}$ are cationic amino acids such as Arg, Lys or Orn. The remaining amino acids may include any amino acid, preferably not Glu or Asp; the amino acids may include Phe, Trp, Tyr, Ala, Gly, Ile, Leu, Pro, Val, Cys, Met, Ser, Thr, Asn, Gln, Nal, Arg, Lys, Orn or His. The net positive charge of the peptide at neutral pH is preferably at least +4.

Examples of less preferred peptides except for those peptides modified with a single hydrocarbyl group (which are described above) comprise peptides having at least 5 to 10 amino acid residues. This preference is based upon economical factors in the manufacturing process.

Preferred peptides of the present invention (except for those modified with a single hydrocarbyl group) include:

| | |
|---|---|
| Arg-Arg-Arg | Arg-Phe-Arg |
| Arg-Tyr-Arg | Arg-Ala-Arg |
| Arg-Ile-Arg | Arg-Leu-Arg |
| Arg-Pro-Arg | Arg-Val-Arg |
| Arg-Cys-Arg | Arg-Met-Arg |
| Arg-Ser-Arg | Arg-Thr-Arg |
| Arg-Asn-Arg | Arg-Gln-Arg |
| Arg-Nal-Arg | Arg-Orn-Arg |
| Arg-His-Arg | Arg-Lys-Arg |
| Arg-Gly-Arg | Arg-Arg-Nal |
| Arg-Arg-Phe | Arg-Arg-Tyr |
| Arg-Arg-Ala | Arg-Arg-Ile |
| Arg-Arg-Leu | Arg-Arg-Pro |
| Arg-Arg-Val | Arg-Arg-Cys |
| Arg-Arg-Met | Arg-Arg-Ser |
| Arg-Arg-Thr | Arg-Arg-Asn |
| Arg-Arg-Gln | Arg-Arg-Lys |
| Arg-Arg-His | Arg-Arg-Orn |
| Arg-Arg-Gly | |

The most preferred peptides of the present invention (except those modified with a single hydrocarbyl group) are short peptides including:

| Arg Lys Orn | |
|---|---|
| Arg-Arg | Arg-Phe |
| Arg-Tyr | Arg-Ala |
| Arg-Ile | Arg-Leu |
| Arg-Pro | Arg-Val |
| Arg-Cys | Arg-Met |
| Arg-Ser | Arg-Thr |
| Arg-Asn | Arg-Gln |
| Arg-Nal | Arg-His |
| Arg-Gly | Phe-Arg |
| Tyr-Arg | Ala-Arg |
| Ile-Arg | Leu-Arg |
| Pro-Arg | Val-Arg |
| Cys-Arg | Met-Arg |
| Ser-Arg | Thr-Arg |
| Asn-Arg | Gln-Arg |
| Nal-Arg | His-Arg |
| Gly-Arg | |

The peptides of the present invention can be synthesized in any manner known in the art. The methods of synthesis may include, but are not limited to, solid-phase, aqueous phase, enzymatic or recombinant processes.

The peptide of the present invention may be synthesized by solid-phase synthesis as described originally by Merrifield in pages 2149–2154 of *J. Amer. Chem. Soc.*, vol. 85, 1963, and may be modified according to PEPTIDES: SYNTHESIS, STRUCTURES AND APPLICATIONS, Gutte B. (ed.), Academic Press, NY, 1995, and CHEMICAL APPROACHES TO THE SYNTHESIS OF PEPTIDES AND PROTEINS, Lloyd-Williams P., Alberico F., Giralt E. (eds.), CRC Press, NY, 1997. Generally, the C-terminal amino acid (with protected N-terminus) is attached to an appropriate solid support via the α-carboxyl group. The N-terminus is protected by an appropriate protecting group (such as tert-butyloxycarbonyl [Boc] or 9-fluorenylmethoxycarbonyl [Fmoc]). An example of a resin is a copolymer of styrene and 1% divinylbenzene. The N α-protecting group is removed, and the amino acid that is N-terminal to the attached amino acid is coupled to the attached amino acid using appropriate coupling reagents (such as dicyclohexylcarbodiimide). The peptide is elongated by repeating the deprotection and coupling steps. When all of the amino acids have been added, side-chain protecting groups used during the synthesis are removed, and the peptide is cleaved from the resin. An hydrocarbyl chain may be attached by a condensation reaction with the Nα-amide of the N-terminal amino acid of a peptide or to the C-terminal amide of the peptide. The hydrocarbyl chain is added after removal of the Fmoc-group and prior to side chain deprotection. Acetic anhydride may also be used for N-terminal acetylation. For a C-terminal amide, an appropriate amide-containing resin is chosen such that when the peptide is cleaved from the resin, the amide group is retained on the peptide. Common solid supports for the synthesis of peptide amides are benzhydrylamide derivatives, such as 4-methylbenzhydrylamine resin. The peptide amide can be cleaved from the resin using hydrogen fluoride.

The peptides can be synthesized individually using an automated synthesizer or using a parallel synthesis approach, such as the tea bag method of simultaneously synthesizing equimolar amounts of multiple peptides as described in U.S. Pat. No. 5,504,190. Other methods of solid-phase synthesis known in the art may also be used to synthesize the peptides of the present invention.

The peptide of the present invention may be synthesized by solution-phase synthesis according to CHEMICAL APPROACHES TO THE SYNTHESIS OF PEPTIDES AND PROTEINS, Lloyd-Williams P., Alberico F., Giralt E. (eds.), CRC Press, NY, 1997. Amino acids are protected and coupled using methods similar to that used for solid-phase synthesis, except that the C-terminus of the C-terminal amino acid must also be protected (common C-terminal protecting groups are alkyl and aryl esters). The coupling reagents may be chemicals such as dicyclohexylcarbodiimide or enzymes such as those supplied by Altus Biologics Inc. (Cambridge, Mass.).

The peptide of the present invention may be synthesized by recombinant synthesis. An oligonucleotide is synthesized using a DNA synthesizer. The sequence of the oligonucleotide encodes the amino acid sequence of the peptide and the codon usage is determined by the organism into which the DNA probe will be cloned. The DNA is then cloned into an appropriate expression vector, which is then introduced into a host organism for expression of the cloned sequence and production (or overproduction) of the peptide. The host organism may be a microorganism such as a bacterium or fungus, virus or bacteriophage, plant or animal. The peptide may be made as a fusion protein to facilitate expression/production or aid in peptide delivery to target. Following purification of the peptide, N- and/or C-terminal hydrocarbyl groups may be added by appropriate methods.

The peptides of the present invention may be purified by conventional liquid chromatographic methods known in the art. These include the use of gel filtration and reverse-phase chromatography.

Without further elaboration, it is believed that one skilled in the art can, using the preceding description, utilize the present invention to its fullest extent.

The following provides examples of the invention. Examples 1–5, 20, 24, 25, and 27 are actual examples; Examples 6–19, 21–23, 26 and 28 are prophetic. These examples are merely illustrative of the invention and are not intended to limit the scope of the disclosure or any claim.

EXAMPLES

Example 1

Materials and Methods of Peptide Synthesis and Bacterial Assays

Synthesis of Peptides

The modified peptides of the present invention were synthesized via solid-phase synthesis by C S Bio Co. (San Carlos, Calif.) and Multiple Peptide Systems (San Diego, Calif.) according to the methods discussed above. However, the modified peptides of the present invention may also be synthesized by any known method in the art.

Antimicrobial Assays

Cultures were grown for 19 h in an incubator shaker (200 rpm; Model G-25, New Brunswick Scientific, Edison, N.J.). The cultures were centrifuged (20 min, 22° C., 2890×g, Labofuge A, American Scientific Products, Houston, Tex.) and resuspended in Wilson's Salts solution (see below). The assays were performed in 96-well "U"-bottom microtiter plates (Dynatech Laboratories, Inc., Chantilly, Va.) in a total volume of 100 μl. The assay mixture (final concentration) consisted of 0.5× medium, peptide at concentrations of 0 to 500 μg/ml in $H_2O$, and inoculum ($2.5 \times 10^5$ cells/ml). The plates were incubated for 18, 24 or 48 h, and growth of the organisms was determined by measuring the change in optical density at 540 nm (Spectramax 250, Molecular Devices, Sunnyvale, Calif.). The minimum inhibitory concentration (MIC) was calculated based on the concentration of peptide required to inhibit growth by >90%.

To determine if the peptides were bactericidal, assays were performed (100 μl total volume) in small tubes as described above (Cluster Tube System, Corning Costar Products, Acton, Mass.). The tubes were incubated for 3, 18 or 24 h; the contents of each tube was diluted to 1 ml with $H_2O$ and cultures were plated onto Aerobic Petri Film (3M, St. Paul, Minn.) or Yeast Mold Film (3M) for bacteria and yeast, respectively.

Strains and Media

The strains, media and incubation temperatures used were as follows:

| | | |
|---|---|---|
| Burkholderia cepacia ATCC 25416 | 0.5X mTGE | 30° C. |
| Candida albicans ATCC 10231 | Sabouraud Dextrose | 30° C. |
| Escherichia coli ATCC 25922 | 0.5X mTGE | 37° C. |
| Klebsiella pneumoniae ATCC 10031 | 0.5X mTGE | 37° C. |
| Klebsiella pneumoniae ATCC 27736 | 0.5X mTGE | 37° C. |
| Pseudomonas aeruginosa ATCC 10145 | 0.5X mTGE | 37° C. |
| Pseudomonas aeruginosa ATCC 27853 | 0.5X mTGE | 37° C. |
| Pseudomonas aeruginosa FRD1 (G. Sayler, U. Tennessee) | 0.5X mTGE | 30° C. |
| Staphylococcus aureus ATCC 29213 | Nutrient | 37° C. |
| Staphylococcus aureus (MRSA) ATCC 33591 | Nutrient | 37° C. |
| Streptococcus sanguis ATCC 10556 | BHI | 37° C. |
| Streptococcus mutans ATCC 25175 | BHI | 37° C. | mTGE Broth, Nutrient Broth, YM and Sabouraud Dextrose Broth are obtained from Difco (Detroit, Mich.); BHI is obtained from Remel (Lenexa, Kans.). Wilson's Salts solution (pH 7.0) contains (g/l): $K_2HPO_4$, 3.0; $KH_2PO_4$, 1.5; $MgSO_4 \cdot 7\ H_2O$, 0.1; $(NH_4)_2SO_4$, 1.0.

Example 2

Antimicrobial assays were performed against K. pneumoniae and P. aeruginosa, two microorganisms commonly found in industrial cooling systems. Experiments with the tripeptide Arg-Trp-Phe-$NH_2$ indicated that the length of the acyl side chain is an important factor in determining peptide efficacy; the lowest MIC values were obtained with octanoate- and decanoate-modified peptides.

Using octanoyl-Arg-Trp-Phe-$NH_2$ as a model, additional peptides were synthesized to study the effect of amino acid composition on peptide efficacy. Octanoyl-Arg-Trp-$NH_2$ demonstrated the greatest activity; these studies demonstrated that arginine, tryptophan, and a terminal amide (—$NH_2$) group are important for activity. The results of this example are shown in FIG. 1.

Example 3

Peptides were synthesized that were modified C-terminally as well as N-terminally (acyl groups are attached at the α-amino group on the N-terminal amino acid). As observed with octanoyl-Arg-Phe-NH-octyl and octanoyl-Arg-Tyr-NH-octyl, the addition of a second octyl group enhanced efficacy of the peptides (compare to octanoyl-Arg-Phe-$NH_2$ and octanoyl-Arg-Tyr-$NH_2$). Generally, the MIC values for the dioctyl-modified peptides ranged from about 2 to about 15 μg/ml. In addition to studying the effect of a second octyl group, tryptophan (Trp) was replaced by less costly amino acids. The results indicated that the dioctyl peptides did not require tryptophan for efficacy, and that Trp could be replaced by Phe, Tyr, Gly, His, Leu, Ala, Cys, Arg, or Gln with no loss in activity. The results of this example are shown in FIG. 2.

Example 4

The efficacy of selected chemically-modified peptides against clinically and industrially relevant microorganisms was determined. Generally, the 9- and 10-carbon chains exhibited somewhat greater efficacy than the dioctyl chains. Against Candida, peptides containing a single arginine residue were more efficacious than those comprised of two arginine residues. The results of this example are shown in FIG. 3.

Example 5

The efficacy of selected chemically-modified peptides against fungi was determined. Aspergillus niger (ATCC 16888) was grown at 30° C. on V-8 Juice Agar which contained 200 ml of V-8 juice, 3 g of $CaCO_3$, 15 g of agar and tap water to 1000 ml (pH 7.2). The medium was sterilized and poured into 75 $cm^2$ vented cell culture flasks (Corning Incorporated, Corning, N.Y.; 30 ml per flask). Spores were harvested by washing the culture with 5 ml of Wilson's Salts Solution and diluting in Wilson's Salts Solution to $9.4 \times 10^4$ spores/ml [spore number is determined by plating spores onto Yeast Mold Film (3M, St. Paul, Minn.)]. The assays are performed in 96 well "U"-bottom microtiter plates. The assay mixture consisted of 0.5× medium (2× Sabouraud Dextrose Broth, Difco, Detroit, Mich.), peptide at concentrations of 0–500 82 g/ml in 5% DMSO/$H_2O$ and spores ($2.35 \times 10^4$ spores/ml). The plates were incubated for 22 h at 30° C. Growth was determined by measuring the change in optical density at 540 nm. The effect of nonanoyl-R—NH-nonyl was determined on growth of A. niger. Growth was inhibited 98% at concentrations as low as 15.6 μg/ml and 83% at 7.8 μg/ml. Growth was inhibited 43% at 1 μg/ml of peptide.

Example 6

Antibiofouling compositions for water treatment comprise chemically-modified peptides from about 0.001% to about 50% by weight of the total composition. Other components in the antibiofouling compositions (used at 0.1% to 50%) may include:

2-bromo-2-nitropropane-1,3-diol (BNPD)

β-nitrostyrene (BNS)

dodecylguanidine hydrochloride 2,2-dibromo-3-nitrilopropionamide (DBNPA)

glutaraldehyde isothiazolin methylene bis(thiocyanate)

triazines n-alkyl dimethylbenzylammonium chloride trisodium phosphate-based antimicrobials tributyltin oxide oxazolidines tetrakis (hydroxymethyl)phosphonium sulfate (THPS)

phenols chromated copper arsenate zinc or copper pyrithione carbamates sodium or calcium hypochlorite sodium bromide halohydantoins (Br, Cl)

Chlorine rates are based on achieving the appropriate concentration of free halogen. Other components in the composition may include biodispersants (about 0.1% to about 15% by weight of the total composition), water, glycols (about 20–30%) or Pluronic (at approximately 7% by weight of the total composition). The concentration of antibiofouling composition for continuous or semi-continuous use is about 5 to about 70 mg/l.

Example 7

Antibiofouling compositions for industrial water treatment comprise chemically-modified peptides from about 0.001% to about 50% by weight of peptide based on the weight of the total composition. The amount of chemically-modified peptide in antibiofouling compositions for aqueous water treatment may be adjusted depending on the particular peptide and aqueous environment. Shock dose ranges are generally about 20 to about 140 mg/l; the concentration for semi-continuous use is about 0.5× of these concentrations.

| | |
|---|---|
| Octanoyl-Arg-NH-octyl | 0.01–5.0% |
| Glutaraldehyde | 45% |
| Water | 50–55% |

Example 8

Examples of antimicrobial compositions for use as household products include:

A. Powder Automatic Dishwashing Composition

| | |
|---|---|
| Hexanoyl-Arg-Trp-Phe-$NH_2$ | 0.00001–50% |
| nonioinic surfactant | 0.4–2.5% |
| sodium metasilicate | 0–20% |
| sodium disilicate | 3–20% |
| sodium triphosphate | 20–40% |
| sodium carbonate | 0–20% |
| sodium perborate | 2–9% |
| tetraacetylethylenediamine | 1–4% |
| sodium sulphate | 5–33% |
| enzymes, including modified enzymes | 0.0001–0.5% |

B. Non-aqueous Liquid Automatic Dishwashing Composition

| | |
|---|---|
| Octanoyl-Arg-Trp-Phe-$NH_2$ | 0.00001–50% |
| liquid nonionic surfactant | 2–10% |
| alkali metal silicate | 3–15% |
| alkali metal phosphate | 20–40% |
| liquid carrier selected from higher glycols, polyglycols, polyoxides, glycoethers | 25–45% |
| stabilizer (partial ester of phosphoric acid and a $C_{16}$–$C_{18}$ alkanol) | 0.5–7% |
| foam suppressor (silicone) | 0–1.5% |
| enzymes, including modified enzymes | 0.0001–0.5% |

C. Liquid Automatic Dishwashing Composition

| | |
|---|---|
| Decanoyl-Arg-Trp-Phe-$NH_2$ | 0.00001–50% |
| fatty acid ester sulphonate | 0–30% |
| sodium dodecyl sulphate | 0–20% |
| alkyl polyglycoside | 0–21% |
| oleic acid | 0–10% |
| sodium disilicate monohydrate | 18–33% |
| sodium citrate dihydrate | 18–33% |
| sodium stearate | 0–2.5% |
| sodium perborate monohydrate | 0–13% |
| tetraacetylethylenediamine | 0–8% |
| maleic acid/acrylic acid copolymer | 4–8% |
| enzymes, including modified enzymes | 0.0001–0.5% |

D. Laundry Detergent or Hard Surface Cleaner

| | |
|---|---|
| Nonanoyl-Arg-Trp-Phe-$NH_2$ | 0.00001–50% |
| alkyl benzene sulfonic acid | 1–20% |
| sodium C12–15 alkyl sulfate | 0.5–5% |
| ethoxylated C14–15 alkyl sulfate | 0–15% |
| C12 glucose amide | 0–15% |
| ethoxylated C12–15 alcohol | 0–15% |
| fatty acid | 1–15% |
| citric acid | 2–15% |
| $C_{12-14}$ alkenyl substituted succinic acid | 0–15% |
| sodium hydroxide | 0.5–15% |
| ethanol | 1–10% |
| monoethanolamine | 0–10% |
| 1,2-propanediol | 2–10% |
| LipolaseR (100 KLU/g commercial solution) | 0–1% |

Example 9

Examples of pharmaceutical compositions for prophylactic or therapeutic treatment include:

| | | |
|---|---|---|
| A. | For Vaginal Douches: | |
| | Naphthoyl-Arg-Trp-Phe-$NH_2$ | 0.000001–20% |
| | bezalkonium chloride, parabens or chlorothymol (other antimicrobial agents) | 0–30% |
| | phenol or menthol (anesthetic or antipruritics) | 10–30% |
| | potassium alum (astringent) | 0.4% or 4 g |
| | zinc sulfate (astringent) | 0.4% or 4g |
| | liquefied phenol | 0.5–5% |
| | glycerin | 10–15% |
| | sodium lauryl sulfate (surface active agent) | 20–50% |
| | sodium borate, sodium bicarbonate or citric acid (pH altering chemicals) | 10–15% |
| | pyrogen-free, sterile water | qs to make 1000 ml |
| B. | For Nasal Solutions | |
| | Naphthylacetyl-Arg-Trp-Phe-$NH_2$ | 0.000001–10% |
| | chlorobutanol | 0.5–5% |
| | sodium chloride | 0.5–5% |
| | antimicrobial preservatives | 0–70% |
| | pyrogen-free, sterile water | qs to make 100 ml |
| C. | Exilirs | |
| | Octanoyl-Arg-Trp-Cys-$NH_2$ | 0.000001–15% |
| | orange oil | 0.1–5% |
| | benzaldehyde | 0.005–5% |
| | sorbitol solution USP | 10–25% |
| | propylene glycol | 40–60% |
| | alcohol | 40–60 % |
| | pyrogen-free, sterile water | qs to make 100 ml |
| D. | Otic Solutions | |
| | Octanoyl-Arg-NH—$CH_2$—$C_6H_5$ | 0.000001–10% |
| | starch glycerin | 10–35% |
| | benzoic acid | 2–10% |
| | glycerin | 70% |
| | pyrogen-free, sterile water | 20% |
| E. | For Inhalations and Inhalants (Solutions) | |
| | Octanoyl-Arg-Trp-$NH_2$ (solubilized) | 0.000001–25% |
| | antioxidants (ex: ascorbic acid) | 0.5–10% |
| | solvent blends (ex: water, ethanol, glycols) | 40–70% |
| | propellants | 5–15% |
| F. | For Inhalations and Inhalants (Suspensions) | |
| | Octanoyl-Arg-NH-octyl (micronized & suspended) | 0.000001–25% |
| | dispersing agent (ex: sorbitan trioleate, oleyl alcohol, oleic acid, lecithin) | 40–50% |
| | propellants | 5–20% |
| G. | Liniments | |
| | Octanoyl-Lys-NH-octyl | 0.000001–20% |
| | ammonium chloride | 10–25% |
| | dilute ammonia solution | 2–20% |
| | oleic acid | 5–25% |
| | turpentine oil | 15–35% |
| | pyrogen-free, sterile water | 50–70% |
| H. | For Water in Oil in Water Emulsion (W/O/W) | |
| | Heptanoyl-Arg-NH-heptyl | 0.000001–20% |
| | isopropyl myristate | 30–60% |
| | sorbitan monooleate | 1–10% |
| | pyrogen-free, sterile water | qs to 100 ml |
| I. | Oil in Water in Oil Emulsion (O/W/O) | |
| | Nonanoyl-Arg-NH-nonyl | 0.000001–20% |
| | soybean oil | 5–20% |
| | ethanol | 10–35% |
| | egg phosphatides | 0.5–10% |
| | Myrj 52 (polyoxyethylene derivative of fatty acids) | 0.1–5% |
| | pyrogen-free, sterile water | qs to 100 ml |
| J. | Water in Oil Microemulsion (W/O) | |
| | Decanoyl-Arg-NH-decyl | 0.000001–20% |
| | propylene glycol esters of capric/caprylic acids | 5–50% |
| | polyoxyethylene (50) sorbitan esters | 8–20% |
| | polyoxyethyleneglycerol triricinoleate | 8–20% |
| | propylene glycol | 20–30% |
| K. | Gels | |
| | Octanoyl-Arg-Ala-NH-octyl | 0.00001–20% |
| | sodium alginate (gelling agent) | 2–10% |
| | glycerin | 2–10% |
| | methyl hydroxybenzoate | 0.1–5% |

-continued

| | | |
|---|---|---|
| | pyrogen-free, sterile water | qs to 100 ml |
| L. | Creme-Lotions | |
| | Octanoyl-Arg-Cys-NH-octyl | 0.01–15% |
| | anhydrous lanolin | 15–40% |
| | mineral oil | 5–35% |
| | olive oil | 5–35% |
| | ethyl alcohol | 5–35% |
| | pyrogen-free, sterile water | 5–20% |
| | glycerin | 5–20% |
| | Tween 80 | 0.5–5% |
| | Polyvinylpyrrolidone (PVP) | 0.5–5% |
| | sodium dodecyl sulfate | 0.1–5% |
| M. | Oleaginous Base Topical Formulations | |
| | Octanoyl-Arg-Phe-NH-octyl | 0.01–5% |
| | anhydrous lanolin | 10–40% |
| | mineral oil | 10–40% |
| | olive oil | 10–40% |
| | Tween 80 | 5–20% |
| N. | Oleaginous Base Ointments | |
| | Octanoyl-Arg-Gly-NH-octyl | 0.01–10% |
| | anhydrous lanolin | 10–45% |
| | white petrolatum | 10–45% |
| | olive oil | 10–45% |
| | Tween 80 | 5–35% |
| O. | Intravenous Admixtures | |
| | Octanoyl-Arg-His-NH-octyl | 0.000001–10% |
| | polyoxyethylene glycol monoester of saturated hydroxylated fatty acid | 5–75% |
| | polyethylene glycol | 2–50 ml |
| | 96 % ethanol | qs 100 ml |
| | solution diluted with isotonic saline, glucose, dextran, fructose or mannitol solution. | |
| P. | Other Parenteral Admixtures | |
| | Octanoyl-His-Arg-NH-octyl | 0.00001–10% |
| | soybean oil | 5–35% |
| | acetylated monoglycerides | 1–25% |
| | egg yolk phosphatides | 0.1–10% |
| | glycerol | 0.1–10% |
| | pyrogen-free, sterile water | qs 100 ml |
| Q. | Opthalmic Solutions | |
| | Octanoyl-Arg-Leu-NH-octyl | 0.000001–10% |
| | sodium chloride USP | 0.5–10% |
| | benzalkonium chloride | 1:10,000 |
| | pyrogen-free, sterile water | qs 100 ml |
| R. | Topical ointments | |
| | Octanoyl-Arg-Asn-NH-octyl | 0.00001–20% |
| | methylparaben | 0.1–10 g |
| | propylparaben | 0.1–10 g |
| | sodium lauryl sulfate | 5–25% |
| | propylene glycol | 5–25% |
| | stearyl alcohol | 10–45% |
| | white petrolatum | 10–45% |
| | pyrogen-free, sterile water | 20–60% |
| S. | Emulsion type topical solutions | |
| | Octanoyl-Arg-Gln-NH-octyl | 0.0001–20% |
| | transcutol | 5–45% |
| | polyoxyethylene glycolated hydrogenated castor oil | 1–15% |
| | transesterified triglyceride (Labrafil) | 5–35% |
| | glycerol monostearate | 5–40% |
| | white petrolatum | 20–60% |
| T. | Space Spray | |
| | Octanoyl-Arg-Arg-NH-octyl | 2–20% |
| | propellant | 80–98% |
| U. | Surface-coating Spray | |
| | Octanoyl-Arg-Tyr-NH-octyl | 1–75% |
| | propellant | 25–99% |
| V. | Foam Spray (edible) | |
| | Octanoyl-Arg-Arg-Arg-NH-octyl | up to 50% |
| | vegetable oil (ex: peanut, cottonseed, soybean) | 40–90% |
| | emulsifier (ex: glyceryl monostearate) | 1–10% |
| | propellant (ex: propane) | 1–10% |
| W. | Other foam Spray | |
| | Heptanoyl-Arg-Arg-NH-heptyl | up to 50% |
| | ethanol | 46–66% |
| | surfactant (ex: nonionic, anionic or cationic) | 0.5–5% |
| | pyrogen-free, sterile water | 28–42% |
| | propellant (ex: propane) | 3–15% |
| X. | Soft gelatin capsules | |
| | Nonanoyl-Arg-Arg-NH-nonyl | 0.0001–15% |

| -continued | |
|---|---|
| caprylic acid | 2–25% |
| capric acid | 2–25% |
| lauric acid | 5–50% |
| myristic acid | 2–25% |
| palmitic acid | 5–15% |
| stearic acid | 5–15% |
| monoacylglyceride | 5–50% |
| diacylglyceride | 5–40% |
| triacylglyceride | 5–60% |
| silicon dioxide | 0.05–3% |
| Y. Hard gelatin capsules | |
| Decanoyl-Arg-Arg-NH-decyl | 0.0001–60% |
| stearate 1500 | 15–30% |
| Eudragit S 100 | 25–69% |

Example 10

Examples of doses of pharmaceutical compositions comprising chemically-modified peptides include:

| | | |
|---|---|---|
| A. | Nebulizer | 5 to 200 mg/ml |
| B. | Metered dose inhaler | 0.5 to 45 mg |
| C. | Dry powder inhaler | 0.5 to 45 mg |
| D. | Intramuscular, intravenous or intraperitoneal injection | 1 to 10 mg/kg |

Example 11

Examples of diseases or infections treatable by pharmaceutical compositions comprising chemically-modified peptides include:

| PEPTIDE | DISEASE/INFECTIONS | DOSE |
|---|---|---|
| Octanoyl-Arg-Phe-Phe-Arg-NH-octyl (SEQ ID NO:29) | Cystic fibrosis | 0.5–45 mg (inhaler) |
| Octanoyl-Arg-Trp-Phe-NH$_2$ | Periodontitis | 0.0001–1% (mouth rinse) |
| Decanoyl-Arg-Trp-Phe-NH$_2$ | Urinary tract infection | 0.01–100 mg/kg (oral) |
| Nonanoyl-Arg-NH-nonyl | Otitis media | 0.000001–20% (ear drops) |
| Octanoyl-Arg-Trp-Cys-NH$_2$ | Acne | 0.001–15% (cream) |
| Nonanoyl-Arg-Arg-NH-nonyl | Gonorrhea | 0.01–100 mg/kg (oral) |
| Octanoyl-Arg-Leu-NH-octyl | Retinitis | 0.000001–5% (eye drops) |
| Octanoyl-Arg-Trp-NH$_2$ | Bronchitis | 0.01–100 mg/kg (oral) |
| Octanoyl-Arg-NH-octyl | Ulcer | 0.01–100 mg/kg (oral) |
| Octanoyl-Lys-NH-octyl | Sinusitis | 0.01–100 mg/kg (oral) |
| Decanoyl-Arg-NH-decyl | Burn or wound infections | 0.000001–20% (cream) |
| Octanoyl-Arg-Arg-NH-octyl | Mononucleosis | 0.01–100 mg/kg (mg/kg, oral) |

Example 12

Examples of hygiene compositions for personal care use comprising chemically-modified peptides include:

| | | |
|---|---|---|
| A. | Facial Cleanser | |
| | Hexanoyl-Arg-Arg-NH-octyl | 0.0001–20% |
| | ammonium laureth sulfate | 28–32% |
| | disodium EDTA | 0.01–0.1% |
| | cocamidopropyl betaine | 6–9% |
| | cocamidopropyl phosphatidyl PG-dimonium chloride | 1–3% |
| | cocamide DEA | 1–3% |
| | lactic acid | 0–3% |
| | glycerin | 1–5% |
| | propylene glycol, imidazolidinyl urea, methylparaben, propylparaben | 0.5–1% |
| | pyrogen-free, sterile deionized water | 50–55% |
| | sodium hydroxide | 0.5–10% |
| B. | Cream | |
| | Octanoyl-Arg-Arg-NH-hexyl | 0.00001–15% |
| | behentrimonium methosulfate, cetearyl alcohol | 0.5–4% |
| | Miglyol 840 | 5–10% |
| | Arlacel 165 | 5–12% |
| | phenyl trimethicone | 0.5–4% |
| | glycerin | 0.5–6% |
| | propylene glycol, diazolidinyl urea, methylparaben, propylparaben | 0.5–2% |
| | xanthan gum | 0.05–2% |
| | magnesium aluminum silicate | 0.05–5% |
| | silica | 0.05–3% |
| | Tween 60 | 0.05–2% |
| | lactic acid | 1–20% |
| | sodium hydroxide | 0.5–12% |
| | cyclomethicone | 0.5–2% |
| | pyrogen-free, sterile deionized water | 30–70% |
| C. | Cream | |
| | Octanoyl-Lys-Arg-NH-octyl | 0.00001–15% |
| | cetostearyl alcohol | 0.3–15% |
| | hydrogenated lanolin | 0.5–15% |
| | ethyl p-hydroxybenzoate | 0.03–5% |
| | polyoxyethylene (20) sorbitan monopalmitate | 0.2–10% |
| | glycerol monostearate | 0.2–10% |
| | sodium N-stearoylglutamate | 0.05–5% |
| | retinol acetate | 0.2–10% |
| | perfume | 0.003–5% |
| | 1,3-butylene glycol | 0.5–15% |
| | polyethylene glycol 1500 | 0.5–15% |
| | pyrogen-free, sterile deionized water balance | |
| D. | Sun-screening Cream | |
| | Octanoyl-Arg-Phe-Phe-Arg-NH-octyl (SEQ ID NO:29) | 0.00001–15% |
| | decamethylcyclopentasiloxane | 3–50% |
| | liquid paraffine | 0.5–15% |
| | polyoxyalkylene-modified organopolysiloxane | 0.1–5% |
| | distearyldimethylammonium chloride | 0.06–5% |
| | perfume | 0.03–5% |
| | titanium oxide | 1–25% |
| | zinc oxide | 0.5–15% |
| | talc | 0.2–15% |
| | glycerin | 0.5–20% |
| | magnesium aluminum silicate | 0.1–10% |
| | pyrogen-free, sterile deionized water balance | |
| E. | Lotion | |
| | Octanoyl-Arg-Trp-Phe-NH$_2$ | 0.00001–20% |
| | magnesium aluminum silicate | 0.2–0.5% |
| | xanthan gum | 0.1–0.3% |
| | glyceryl stearate, PEG-100 stearate | 5–10% |
| | Tween 60 | 0.5–2% |
| | ceteareth alcohol | 0.5–2% |
| | propylene glycol, diazolidinyl urea, methylparaben, propylparaben | 0.5–2% |
| | glycerin | 2–6% |
| | Miglyol 840 | 8–12% |
| | phenyl trimethicone | 1–3% |

|   |   |   |
|---|---|---|
|   | -continued | |
|   | cyclomethicone | 0.5–2% |
|   | lactic acid | 1–20% |
|   | sodium hydroxide | 0.5–13% |
|   | pyrogen-free, sterile deionized water | 35–38% |
| F. | Clear Lotion | |
|   | Decanoyl-Arg-Trp-Phe-NH$_2$ | 0.00001–15% |
|   | tocopherol acetate | 0.001–5% |
|   | glycerin | 0.4–10% |
|   | 1,3-butylene glycol | 0.4–10 |
|   | ethanol | 0.8–15% |
|   | polyoxyethylene (60) hardened castor oil | 0.05–5% |
|   | methyl p-hydroxybenzoate | 0.02–5% |
|   | citric acid | 0.005–5% |
|   | sodium citrate | 0.01–5% |
|   | perfume | 0.005–5% |
|   | pyrogen-free, sterile deionized water balance | |
| G. | Milky Lotion | |
|   | Naphthoyl-Arg-Trp-Phe-NH$_2$ | 0.00001–15% |
|   | stearic acid | 0.15–5% |
|   | cetyl alcohol | 0.05–5% |
|   | polyoxyethylene (10) monooleate | 0.2–10% |
|   | L-arginine | 0.03–6% |
|   | sodium L-glutamate | 0.002–5% |
|   | PCA-NA | 0.005–5% |
|   | 2-aminoethylthiosulfonic acid | 0.02–5% |
|   | 2-aminoethylsulfinic acid | 0.001–5% |
|   | propylene glycol | 0.5–10% |
|   | glycerin | 0.3–10% |
|   | ethanol | 0.3–10% |
|   | ethyl p-hydroxybenzoate | 0.03–3% |
|   | perfume | 0.003–3% |
|   | carboxyvinyl polymer | 0.01–5% |
|   | pyrogen-free, sterile deionized water balance | |
| H. | Sun-screening Milky Lotion | |
|   | Naphthylacetyl-Arg-Trp-Phe-NH$_2$ | 0.00001–15% |
|   | stearic acid | 0.2–5% |
|   | cetyl alcohol | 0.05–5% |
|   | liquid paraffin | 1–20% |
|   | polyoxyethylene (10) oleate | 0.1–5% |
|   | sorbitan trioleate | 0.1–5% |
|   | perfume | 0.02–2% |
|   | 1,3-butylene glycol | 0.5–5% |
|   | dipropylene glycol | 0.3–3% |
|   | carboxyvinyl polymer | 0.01–5% |
|   | trisodium edetate | 0.005–3% |
|   | triethanolamine | 0.04–5% |
|   | silica | 0.2–2% |
|   | talc | 0.2–2% |
|   | titanium oxide | 0.3–3% |
|   | zinc oxide | 0.3–3% |
|   | pyrogen-free, sterile deionized water balance | |
| I | Hair Conditioner | |
|   | Octanoyl-Arg-Trp-Cys-NH$_2$ | 0.001–20% |
|   | pyrogen-free, sterile deionized water | 89–92% |
|   | dimethyl hydroxymethyl pyrazole | 0.5–5% |
|   | panthenol | 0.1–0.3% |
|   | disodium EDTA | 0.02–.1% |
|   | cetearyl alcohol, ceteareth-20 | 1–2% |
|   | stearyl alcohol | 4–6% |
|   | cetrimonium bromide | 4–6% |
|   | jojoba oil | 0.2–0.5% |
|   | acetamide MBA | 0.5–2% |
|   | lactamide MEA | 0.5–2% |
| J. | Hair Shampoo | |
|   | Octanoyl-Arg-Trp-NH$_2$ | 0.001–20% |
|   | anionic surfactant (polyoxyethylenealkyl sulfate) | 5–15% |
|   | cationic surfactant (distearyl dimethylammonium chloride) | 0.5–2.5% |
|   | amphoteric surfactant (alkylamine oxide) | 5–15% |
|   | thickener (isostearic acid diethanolamide) | 0.5–15% |
|   | wetting agent (propylene glycol) | 1–20% |
|   | lower alcohol (ethanol) | 1–15% |
|   | perfume | proper amount |
|   | pyrogen-free, sterile deionized water balance | |

-continued

| | | |
|---|---|---|
| K. | Antiperspirant/Deodorant Solution | |
| | Octanoyl-Arg-NH-octyl | 0.0001–20% |
| | aluminum chlorohydrate | 10–40% |
| | SD alcohol 40 | 25–35% |
| | Transcutol ethoxydiglycol | 5–10% |
| | Tween 20 | 0.5–1% |
| | cocamidopropyl phosphatidyl PG-dimonium chloride | 1–2% |
| | pyrogen-free, sterile deionized water | 20–25% |
| L. | Mouthwash | |
| | Octanoyl-Lys-NH-octyl | 0.001–20% |
| | SD alcohol | 4–35% |
| | selenomethionine | 0.2–5% |
| | calcium gluconate | 0.25–5% |
| | L-glutathione | 0.10–4% |
| | xylitol-sweetener | 1–10% |
| | coloring agents | 0.1–3% |
| | flavoring agents | 0.1–5% |
| | pyrogen-free, sterile deionized water | balance |
| M. | Toothpaste | |
| | Heptanoyl-Arg-NH-heptyl | 0.00001–10% |
| | glycerol | 2–50% |
| | magnesium carbonate | 0.35–10% |
| | sodium fluoride | 0.35–10% |
| | zinc acetate | 0.05–10% |
| | L-glutathione | 0.01–5% |
| | L-selenomethionine | 0.005–5% |
| | ascorbic acid | 0.15–5% |
| | N-acetylcysteine | 0.01–10% |
| | benzalkonium chloride | 0.01–10% |
| | polyvinyl pyrrolidone | 0.75–10% |
| | xylitol (sweetner) | 0.025–5% |
| | coloring agent | 0.02–3% |
| | peppermint (flavor) | 0.02–3% |
| | pyrogen-free, sterile deionized water | balance |
| N. | Tooth gels | |
| | Nonanoyl-Arg-NH-nonyl | 0.00001–10% |
| | glycerin | 2–50% |
| | poloxamer | 10–25% |
| | ascorbic acid | 0.15–5% |
| | sodium lauryl sulfate | 0.12–12% |
| | peppermint oil | 0.1–5% |
| | alpha tocopherol | 0.075–8% |
| | calcium laurate | 0.025–5% |
| | selenomethionine | 0.02–5% |
| | sodium fluoride | 0.02–5% |
| | L-glutathione | 0.01–10% |
| | coloring agent | 0.01–5% |
| | xylitol (sweetner) | 0.15–20% |
| | zinc acetate | 0.015–3% |
| | pyrogen-free, sterile deionized water | balance |
| O. | Body Washes | |
| | Decanoyl-Arg-NH-decyl | 0.001–20% |
| | dimethylsiloxane-methyl siloxane copolymer | 0.5–2.5% |
| | potassium cocoyl hydrolyzed collagen | 5–40% |
| | coconut oil potassium soap (40%) | 0.5–15% |
| | coconut oil fatty acid diethanolamide | 1–15% |
| | lauric acid diethanolamide | 1–15% |
| | p-hydroxybenzoates and phenoxyethanol | 0.05–2.5% |
| | pyrogen-free, sterile deionized water | balance |
| P. | Ointment | |
| | Octanoyl-Arg-Ala-NH-octyl | 0.00001–20% |
| | tocopherol acetate | 0.05–5% |
| | retinol palmitate | 0.1–10% |
| | stearyl alcohol | 1–30% |
| | Japan wax | 2–40% |
| | polyoxyethylene (10) monooleate | 0.025–5% |
| | glycerol monostearate | 0.03–10% |
| | vaseline | 5–45% |
| | pyrogen-free, sterile deionized water | balance |

Example 13

Examples of cosmetic formulations comprising chemically-modified peptides of the present invention include:

A. Liquid Makeup Foundation

| | |
|---|---|
| Octanoyl-Arg-Cys-NH-octyl | 0.000001–10% |
| isostearyl neopentanoate | 4–6% |
| isocetyl stearate | 5–10% |
| triisocetyl citrate | 3–6% |
| Generol 122E | 1–3% |
| glyceryl stearate | 1–3% |
| Generol 122 | 0.5–3% |
| dimethicone | 0.5–3% |
| propylparben | 0.5–0.15% |
| cocamido propyl betaine | 0.5–2% |
| disodium oleamido PBG sulfosuccinate | 0.5–1% |
| magnesium aluminum silicate | 0.1–0.5% |
| xanthan gum | 0.1–0.5% |
| propylene glycol | 3–6% |
| glycerin | 1–3% |
| disodium EDTA | 0.05–0.1% |
| imidazolidinyl urea | 0.2–0.3% |
| methylparaben | 0.1–0.3% |
| sodium dehydroacetate | 0.05–0.2% |
| lactic acid | 0–5% |
| pyrogen-free, sterile deionized water | 45–60% |
| iron oxides | 1–3% |
| titanium dioxide | 5–10% |
| sodium hydroxide or citric acid q.s. to pH | 5–5.5 |

B. Foundation

| | |
|---|---|
| Octanoyl-Arg-Phe-NH-octyl | 0.001–5 parts |
| mica | 6–60 parts |
| talc | 4–40 parts |
| titanium dioxide | 0.1–3 parts |
| calcium phosphate | 0.5–7 parts |
| brown iron oxide | 0.5–5 parts |
| yellow iron oxide | 0.001–1 part |
| red iron oxide | 0.05–5 parts |
| black iron oxide | 0.05–5 parts |

C. Creamy Lipstick Formulation

| | |
|---|---|
| Octanoyl-Arg-Gly-NH-octyl | 0.000001–5% |
| castor oil | 30–40% |
| isopropyl lanolate | 5–15% |
| mica | 4–6% |
| titanium dioxide | 3–6% |
| iron oxides | 0.5–4% |
| FD & C colors | 3–7% |
| isopropyl lanolate | 8–15% |
| Candelilla wax | 7–10% |
| isostearyl neopentanoate | 3–10% |
| beeswax | 0.5–5% |
| microcrystalline wax | 0.5–5% |
| carnauba wax | 0.4–1% |
| propylparaben | 0.05–3% |
| BHT | 0.01–0.1% |
| tocopherol | 0.05–0.5% |

D. Eyeshadow

| | |
|---|---|
| Octanoyl-Arg-His-NH-octyl | 0.0001–5 g |
| talc | 8–100 g |
| aluminum stearate | 0.6–15 g |
| zinc stearate | 0.6–15 g |
| ultramarine blue | 0.5–15 g |
| black iron oxide | 0.01–5 g |
| chromium hydroxide green | 0.2–5 g |
| yellow iron oxide | 0.05–5 g |

E. Blush

| | |
|---|---|
| Octanoyl-His-Arg-NH-octyl | 0.0001–5 g |
| sericite | 4–50 g |
| talc | 2–35 g |
| mica | 1–20 g |
| kaolin | 0.5–10 g |

-continued

| | |
|---|---|
| aluminum stearate | 0.6–15 g |
| red iron oxide | 0.4–10 g |
| black iron oxide | 0.01–2 g |
| brown iron oxide | 0.8–16 g |
| yellow iron oxide | 0.02–5 g |
| titanium dioxide | 0.4–5 g |

Example 14

Examples of chemically-modified peptide compositions for medical devices include:

A. Polyurethane Adhesive Film Containing Pharmaceutical Composition

| | |
|---|---|
| Octanoyl-Arg-Leu-NH-octyl | 0.025–20% |
| polyoxyethylene glycol | 2–5% |
| polyurethane adhesive solution | 10–25% | when coated and dried results in a tacky, adhesive film for dressing wounds

B. Suture Containing Pharmaceutical Composition

| | |
|---|---|
| Octanoyl-Arg-Asn-NH-octyl | 0.025–20% |
| polyoxyethylene glycol | 2–5% | suture is dipped in solution above and excess is wiped away with a paper towel for dressing wounds C. Catheter Containing Pharmaceutical Composition

| | |
|---|---|
| Octanoyl-Arg-Gln-NH-octyl | 0.025–20% |
| polyoxyethylene glycol | 2–5% | solution above is applied onto the surface of polyurethane catheter

D. Foam Dressing Containing Pharmaceutical Composition

| | |
|---|---|
| Octanoyl-Arg-Arg-NH-octyl | 0.025–20% |
| polyoxyethylene glycol | 2–5% |

3.5 g of above solution is mixed with 5.5 g polyurethane prepolymer and then 5.5 g water to form a foam which is dried and then sliced to produce foam dressings E. Hydrocolloid Dressing Containing Pharmaceutical Composition

| | |
|---|---|
| Octanoyl-Arg-Tyr-NH-octyl | 0.025–20% |
| polyoxyethylene glycol | 2–5% |

2 g of above solution is mixed with 4 g sodium carboxymethyl cellulose and then 4 g polyurethane prepolymer. Mixture is pressed between a polyurethane film and silicone-treated polyester liner to make a 2.5 mm thick treated hydrocolloid matrix which is allowed to cure for 24 hours.

Example 15

Examples of chemically-modified peptide compositions for use in animal feed include:

A.

| | |
|---|---|
| Octanoyl-Arg-Arg-Arg-NH-octyl | 0.01–5% |
| corn silage | 5–35% |
| alfalfa silage | 1–30% |
| alfalfa hay | 1–25% |
| ground barley | 1–20% |
| ground corn | 5–15% |
| soybean meal | 10–65% |

B.

| | |
|---|---|
| Heptanoyl-Arg-Arg-NH-heptyl | 0.01–5% |
| corn silage | 5–35% |
| alfalfa silage | 1–30% |
| alfalfa hay | 1–25% |
| ground barley | 1–20% |
| ground shelled corn | 5–15% |
| calcium salts of palm oil | 0.5–5% |
| dry molasses | 0.5–5% |
| ammonium phosphate | 0.1–5% |
| mineral mix (including vitamins A, D, and E; magnesium oxide, selenium, magnesium and potassium sulfate) | 0.5–10% |

Example 16

Examples of chemically-modified peptides useful as a food preservative against microbes such as *Salmonella typhimurium* and *Clostridium botulinum* include:

| PEPTIDE | MIC ($\mu$g/ml) |
|---|---|
| Octanoyl-Arg-Ala-NH-octyl | $\leq$15 |
| Octanoyl-Arg-Cys-NH-octyl | $\leq$15 |
| Octanoyl-Arg-Phe-NH-octyl | $\leq$8 |
| Octanoyl-Arg-Arg-NH-octyl | $\leq$4 |
| Octanoyl-Arg-Trp-Phe-NH$_2$ | $\leq$15 |
| Octanoyl-Arg-Trp-NH$_2$ | $\leq$15 |
| Nonanoyl-Arg-NH-nonyl | $\leq$4 |
| Octanoyl-Lys-Arg-NH-octyl | $\leq$4 |

Example 17

Peptide Compositions for Textiles

Chemically-modified peptides can be applied by coating or spinning effective amounts of peptide onto or into the desired polymer. The peptides may be prepared in an aqueous solution to use as a coating solution or combined with a polymer. The coating solutions may contain small water-soluble molecules that do not interfere with the antimicrobial action of the peptide. A peptide and polymer solution or mixture may be made and undergo casting or formation to the desired shaped article, fiber or film. The shaped article, fiber or film may then be quenched in water or methanol, allowed to air dry or dry under an appropriate atmosphere to prevent oxidative reactions.

| | |
|---|---|
| Peptide | 0.01–15% |
| Polymer solution (e.g., containing wool or cotton) | 10%–15% |

The resulting solution may be placed into a microscale spinning apparatus and fiber is formed while wet with methanol. The antimicrobial activity of the peptides may be tested in tubes containing LB media innoculated with the peptide-containing fiber and *E. coli* growing at log phase ($1\times10^6$ to $1\times10^7$ cells/ml). Aliquots can be taken from the culture tube at periodic intervals and absorbance readings at 600 nm (uv/vis) can be measured in a microcuvette.

| Peptides | MIC ($\mu$g/ml) |
|---|---|
| Octanoyl-Arg-Trp-Phe-NH$_2$ | 15 |
| Octanoyl-Arg-Arg-NH-octyl | $\leq$8 |
| Octanoyl-Arg-Phe-Phe-Arg-NH-octyl (SEQ ID NO:29) | $\leq$4 |
| Decanoyl-Arg-NH-decyl | $\leq$15 |
| Octanoyl-Arg-Trp-NH$_2$ | $\leq$15 |
| Nonanoyl-Arg-Arg-NH-nonyl | $\leq$2 |

Example 18

Examples of chemically-modified peptide compositions comprising liposomes include:

A. Composition comprising liposomes and Octanoyl-Arg-Trp-NH$_2$ for inhibition of microbial growth in cell culture at 37° C.

| | |
|---|---|
| Decanoyl-Arg-Arg-NH-decyl | 0.5–50 $\mu$g |
| Liposome (unilamellar or (multilamellar) | 2–400 $\mu$g |

Viable cell counts can be performed after 3 hours to show greater than 90% reduction in growth of *K. pneumonia* and *P. aeruginosa* at or above approximately 8 $\mu$g/ml of Octanoyl-Arg-Trp-NH$_2$ as compared to untreated cultures.

B. Efficacy of composition comprising liposomes and Octanoyl-Arg-Arg-NH-octyl against several clinically and industrially relevant organisms can be determined.

| Organism | MIC ($\mu$g/ml) |
|---|---|
| *C. albicans* ATCC 10231 | $\leq$31 |
| *B. cepacia* ATCC 25416 | $\leq$125 |
| *E. coli* ATCC 25922 | $\leq$3.9 |
| *K. pneumoniae* ATCC 10031 | $\leq$3.9 |
| *P. aeruginosa* ATCC 27853 | $\leq$2 |
| *S. aureus* (MRSA) ATCC 33591 | $\leq$2 |
| *S. aureus* ATCC 29213 | $\leq$3.9 |

Example 19

Examples of peptides modified with N-terminal octanoyl and C-terminal octylamine groups that demonstrate efficacy against *P. aeruginosa* and *K. pneumoniae*.

| PEPTIDE | MIC ($\mu$g/ml) |
|---|---|
| Arg-Trp-Phe-Arg-Arg (SEQ ID NO:30) | $\leq$62 |
| Arg-Trp-Phe-Arg (SEQ ID NO:1) | $\leq$8 |
| Arg-Trp-Arg-Phe (SEQ ID NO:2) | $\leq$15 |
| Arg-Arg-Trp-Phe (SEQ ID NO:4) | $\leq$8 |
| Arg-Phe-Arg-Trp (SEQ ID NO:6) | $\leq$62 |
| Arg-Phe-Trp-Arg (SEQ ID NO:31) | $\leq$8 |
| Arg-Arg-Phe-Trp (SEQ ID NO:7) | $\leq$8 |

-continued

| PEPTIDE | MIC (µg/ml) |
|---|---|
| Trp-Arg-Trp-Phe (SEQ ID NO:32) | ≦31 |
| Arg-Trp-Arg | ≦62 |
| Arg-Phe-Arg | ≦62 |
| Arg-Arg-Trp | ≦31 |
| Arg-Arg-Phe | ≦62 |
| Arg-Phe-Trp | ≦15 |
| Trp-Arg-Phe | ≦500 |
| Trp-Phe-Arg | ≦125 |
| Phe-Trp-Arg | ≦125 |
| Phe-Arg-Trp | ≦500 |
| Phe-Arg | ≦125 |
| Arg-Trp-Tyr | ≦500 |
| Arg-Nal-Phe | ≦62 |
| Arg-Nal-Nal | ≦31 |
| Arg-Trp-Nal | ≦15 |
| Orn-Trp-Phe | ≦15 |

Example 20
Antiviral Susceptibility Testing

The antiviral activity of octanoyl-RR—NH-octyl was determined. The peptide was first evaluated for cytotoxicity. Vero cells (ATCC CCL81) were grown to confluency in 96-well microtiter plates in Eagles Minimal Essential Medium (E-MEM) supplemented with 10% fetal bovine serum (FBS), 100 units/ml penicillin, 2.5 µg/ml Amphotericin B and 10 µg/ml gentamicin (total volume 0.2 ml). Plates were incubated at 37° C. in a humidified atmosphere of 6% $CO_2$. Spent culture medium was removed and each well received 0.2 ml of the appropriate peptide dilution or cell culture medium (cell control wells). The plates were incubated at 37° C., 6% $CO_2$ for 4–8 days, after which the cells were examined microscopically and a microtetrazolium assay was performed using 2,3-bis[(phenylamino)carbonyl]-2H-tetrazolium hydroxide (XTT).

Percent viability of non-infected cells decreased in the presence of octanoyl-RR—NH-octyl to 59.0% at 125 ppm, as compared to cell controls. At concentrations of 62.5 ppm to 3.9 ppm peptide, percent cellular viability ranged from 80.6% to 98.0% of cell controls, indicating no significant cytotoxicity at these concentrations.

The peptide was evaluated for antiviral activity using Herpes Simplex Virus Type 1 in a plaque reduction assay. Microtiter plates (24 well) were seeded with Vero cells to confluency. The supernatant medium was removed by aspiration and each well received 0.5 ml E-MEM with 5% FBS. Virus (0.2 ml) was added to the medium in the test and control wells to achieve 50 plaque-forming units (pfu) per well. After virus attachment, the inoculum was removed and replaced with 1 ml medium containing the appropriate dilution of peptide. Plates were incubated at 37° C. under 6% $CO_2$ until plaques were sufficiently well defined to count (2–5 days). The cells were fixed with formalin (10%) in phosphate buffered saline and stained with crystal violet. Plaques were then counted and the $EC_{50}$ (peptide concentration that produces a 50% reduction in plaque formation) was calculated.

No significant viral inhibition was observed at concentrations up to 62.5 ppm octanoyl-RR—NH-octyl (percent viral inhibition did not exceed 44.9%). Plaque formation could not be determined at concentrations above 62.5 ppm due to cytotoxicity.

Example 21
Antiparasitic Susceptibility Tesing

Methods for antiparasitic susceptibility testing are described in pages 1653–1662 of Antiparasitic agents and susceptibility tests, Nguyen-Dinh, P., Secor, W. E., and Manual of clinical microbiology (7th Edition), Murray, P. R., Baron, E. J., Pfaller, M. A., Tenover, F. C., Yolken, R. H. (eds.), American Society for Microbiology Press, Washington, D.C., 1999.

Testing for Plasmodium Falciparum

P. falciparum is added as parasite-infected red blood cells (at concentrations ranging from 0.05 to 0.5%) to flasks containing 50 ml human red blood cells in RPMI 1640 medium plus [$^3$H]-labeled hypoxanthine (10 µM; 50 µCi) for 150 ml final volume. The red blood cells are incubated for 1 week at 37° C. under 5% $CO_2$. Test peptides (e.g., octanoyl-Arg-Gly-NH-octyl, octanoyl-Arg-Trp-Phe-$NH_2$) are then added at final concentrations of 0 to 500 µg/ml and the mixtures are incubated an additional 24 hr. The cells undergo filtration and hypoxanthine uptake is measured by liquid scintillation counting to determine P. falciparum viability.

Example 22

The hemolytic activity of sample peptides can be determined using human erythrocytes. Assays take place in 96-well flat bottom microtiter plates in a total volume of 100 µl. The assay components (final concentration) are 0.25% human red blood cells (RBCs) and peptide at concentrations of 0 to 500 µg/ml. Plates incubate for 1 hr at 37° C. and then undergo centrifugation at 2800 rpm for 5 min. The supernatant is separated from the pellet and the optical density of the supernatant at 414 nm is measured. The concentration of peptide to lyse 50% of the RBCs is the hemolytic dose (HD) or $HD_{50}$.

Example 23

Efficacy of Octanoyl-R—NH-octyl Against a Commercially Available Consortium of Environmental Bacteria for Determination of Biological Oxygen Demand (BOD)

Polyseed BOD capsules (InterBio; The Woodlands, Tex. 77380) are rehydrated according to manufacturer's instructions. Assays are performed in 96-well "U"-bottom microtiter plates in a total volume of 100 µl. The assay mixture (final concentration) consists of 0.5× Wilson's Salts Solution, peptide at 0 to 87.5 µg/ml in $H_2O$, approximately 1×10$^6$ cells and 0.3 µCi/ml of $^{14}$C-amino acid mixture. The microtiter plates are incubated for 2 hr at 37° C. Cells are washed onto filter paper, the filter paper is dried and the radioactivity taken up by the cells is determined.

Bacteria were isolated from Polyseed Capsules and were identified according to Biolog Inc. (Hayward, Calif.). The organisms that were identified included Acinetobacter antratus, Acinetobacter lwoffii, Bacillus species, Enterobacter agglomerans, Enterobacter sakazaki, Flavobacterium species, Klebsiella species and Pseudomonas species.

Example 24

Efficacy of Octanoyl-R—NH-octyl Against Bacterial Paper Mill Isolates

Pseudomonas aeruginosa, Xanthomonas maltophila, Comamonas acidivorans and Enterobacter cloacae were isolated directly from paper mill water samples (organisms were identified using the Biolog system). Antimicrobial assays were performed as described above using TGE as the medium. P. aeruginosa, C. acidivorans and E. cloacae were incubated at 30° C., X. maltophila was incubated at 37° C.

| Bacterium | MIC (μg/ml) |
| --- | --- |
| P. aeruginosa | ≦10 |
| X. maltophila | ≦5 |
| C. acidivorans | >313 |
| E. cloacae | >313 |

Example 25

Efficacy of Octanoyl-R—NH-octyl Against Anaerobic Bacteria

*Desulfovibrio desulfuricans* (ATCC 7757) was grown in Modified Baar's Medium for Sulfate Reducers (ATCC Medium 1249) which was prepared under strictly anaerobic conditions. The antimicrobial assay was carried out in 10 ml sealed vials containing 2 ml medium. Peptide was added at final concentrations of 0 to 250 μg/ml in 5% DMSO/95% $H_2O$. The MIC for *D. desulfuricans* was ≦62.5–125 μg/ml.

Example 26

Inhibition of Algal Growth by Octanoyl-R—NH-octyl

*Selenastrum capricornutum* (ATCC 22662) is grown (24° C.) in Gorham's Medium (pH 7.5) which contains: 496 mg/l $NaNO_3$, 39 mg/l $K_2HPO_4$, 75 mg/l $MgSO_4.7H_2O$, 36 mg/l $CaCl2.2H_2O$, 6 mg/l Fe citrate, 58 mg/l $Na_2SiO_3.9H_2O$, 20 mg/l $Na_2CO_3$, 6 mg/l citric acid, 1 mg/l EDTA. Assays are performed in 96-well "U"-bottom microtiter plates in a total volume of 100 μl. The assay mixture (final concentration) consists of peptide at 0 to 22 μg/ml in $H_2O$, approximately $1\times10^5$ cells and 1 μCi/ml of $^{14}C$—$NaHCO_3$ in Tris buffer. The microtiter plates are incubated for 4 hr at 2000 lux (24° C.). The algae are then washed onto filter paper, the filter paper is dried and the radioactivity is measured to determine the amount of $NaHCO_3$ taken up by the cells.

Example 27

Efficacy of Octanoyl-R—NH-octyl Against Bacterial Cooling Tower Isolates

*Bacillus* and *Aeromonas* were isolated directly from water in an industrial cooling tower (organisms may be identified using the Biolog system). Antimicrobial assays were performed as above using TGE as the medium. Microtiter plates were incubated for 18 hr at 35° C. The MIC values for *Bacillus* and *Aeromonas* were 15.6 and 62.5 μg/ml, respectively.

Example 28

Bacterial Membrane Permeabilization by Peptides

The outer membrane permeabilization assay is performed according to the protocol described by Falla et al. (Mode of action of the antimicrobial peptide indolicidin; 1996; Falla, T. J., Karunaratne, D. N., and Hancock, R. E. W.; J. Biol. Chem., 271:19298–19303). Cultures of *E. Coli* and *P. aeruginosa* are grown overnight in LB Broth (Difco). One ml of the overnight culture is transferred to 50 ml of fresh LB Broth and the cells are incubated at 37° C. (200 rpm) to an optical density (OD) of 0.4–0.6 (600 nm). The cells are centrifuged (5000 rpm, 10 min), washed with 50 of buffer (5 mM HEPES, pH 7.2, 5 mM KCN), centrifuged again for 10 min (5000 rpm), and resuspended in buffer to an OD (600 nm) of 0.5. One ml of cells is mixed with 10 μM NPN (1-N-phenylnaphthylamine, 5.0 mM stock solution prepared in 100% acetone), and fluorescence is measured with a fluorescence spectrophotometer (excitation wavelength 350 nm, emission wavelength 420 nm).

Inner membrane permeability is determined using *Agrobacterium tumefaciens* A136 (obtained from Clay Fuqua, Trinity University, San Antonio, Tex.) which exhibits β-galactosidase activity in the presence of select homoserine lactones. The substrate o-nitrophenyl-β-D-galactoside is hydrolyzed by β-galactosidase to yield galactose and o-nitrophenol. *A. tumefaciens* is grown overnight in TGE broth supplemented with 10 nM N-(β-ketocaproyl)-DL-homoserine lactone (Sigma Chemical Company). In the presence of octanoyl-R—NH-octyl, the inner membrane of *A. tumefaciens* is permeabilized, allowing ONPG uptake and hydrolysis by β-galactosidase. Formation of o-nitrophenol can be monitored spectrophotometrically ($A_{420}$).

Although the invention has been described with reference to particular means, materials and embodiments, it is to be understood that the invention is not limited to the particulars disclosed, and extends to all equivalents within the scope of the claims.

What is claimed is:

1. An antimicrobial peptide represented by Formula I:

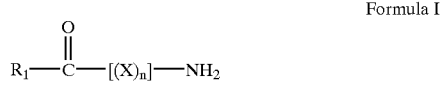

Formula I wherein n=2 and $[(X)_2]$ is Arg-Trp; and wherein $R_1$ is selected from the group consisting of $C_1$–$C_9$ alkyl; and $C_3$–$C_6$ cycloalkyl; and wherein the antimicrobial peptide inhibits the growth of a microbe selected from the group consisting of bacteria, archaea, fungi, algae, protozoa, multicellular parasites and viruses.

2. The antimicrobial peptide of claim 1 wherein said peptide is incorporated into a polymer.

3. The antimicrobial peptide of claim 2 wherein said polymer is selected from the group consisting of a polysaccharide, a glycol polymer, a polyester, a polyurethane, a polyacrylate, a polyacrylonitrile, a polyamide, a polyolefin, a polystyrene, a vinyl polymer, a polypropylene, silk, a biopolymer, and mixtures thereof.

4. A substrate coated with the antimicrobial of claim 1.

5. The substrate of claim 4, wherein the substrate is selected from a group consisting of personal care products, health care products, household products, food preparation surfaces, food packaging surfaces, medical devices, wound dressings, surgical staples, membranes, shunts, surgical gloves, tissue patches, prosthetic devices, wound drainage tubes, blood collection and transfer devices, tracheotomy devices, intraocular lenses, laboratory devices, textile products and painted surfaces.

6. The antimicrobial peptide of claim 1, further comprising a carrier selected from the group consisting of a pharmaceutically acceptable carrier, and industrially acceptable carrier, a household product, and a personal care composition.

7. The antimicrobial peptide of claim 1, wherein the antimicrobial peptide terminates the growth of the mircrobe.

8. The antimicrobial peptide of claim 1, wherein the antimicrobial peptide is administered topically.

* * * * *

SEQUENCE LISTING

<160> NUMBER OF SEQ ID NOS: 32

<210> SEQ ID NO 1
<211> LENGTH: 4
<212> TYPE: PRT
<213> ORGANISM: Artificial Sequence
<220> FEATURE:
<223> OTHER INFORMATION: Novel Sequence

<400> SEQUENCE: 1

Arg Trp Phe Arg
1

<210> SEQ ID NO 2
<211> LENGTH: 4
<212> TYPE: PRT
<213> ORGANISM: Artificial Sequence
<220> FEATURE:

<223> OTHER INFORMATION: Novel Sequence

<400> SEQUENCE: 2

Arg Trp Arg Phe
1

<210> SEQ ID NO 3
<211> LENGTH: 4
<212> TYPE: PRT
<213> ORGANISM: Artificial Sequence
<220> FEATURE:
<223> OTHER INFORMATION: Novel Sequence

<400> SEQUENCE: 3

Arg Trp Trp Arg
1

<210> SEQ ID NO 4
<211> LENGTH: 4
<212> TYPE: PRT
<213> ORGANISM: Artificial Sequence
<220> FEATURE:
<223> OTHER INFORMATION: Novel Sequence

<400> SEQUENCE: 4

Arg Arg Trp Phe
1

<210> SEQ ID NO 5
<211> LENGTH: 4
<212> TYPE: PRT
<213> ORGANISM: Artificial Sequence
<220> FEATURE:
<223> OTHER INFORMATION: Novel Sequence

<400> SEQUENCE: 5

Arg Trp Arg Trp
1

<210> SEQ ID NO 6
<211> LENGTH: 4
<212> TYPE: PRT
<213> ORGANISM: Artificial Sequence
<220> FEATURE:
<223> OTHER INFORMATION: Novel Sequence

<400> SEQUENCE: 6

Arg Phe Arg Trp
1

<210> SEQ ID NO 7
<211> LENGTH: 4
<212> TYPE: PRT
<213> ORGANISM: Artificial Sequence
<220> FEATURE:
<223> OTHER INFORMATION: Novel Sequence

<400> SEQUENCE: 7

Arg Arg Phe Trp
1

<210> SEQ ID NO 8
<211> LENGTH: 4
<212> TYPE: PRT
<213> ORGANISM: Artificial Sequence
<220> FEATURE:
<223> OTHER INFORMATION: Novel Sequence -continued

```
<400> SEQUENCE: 8

Arg Trp Ala Arg
1

<210> SEQ ID NO 9
<211> LENGTH: 4
<212> TYPE: PRT
<213> ORGANISM: Artificial Sequence
<220> FEATURE:
<223> OTHER INFORMATION: Novel Sequence

<400> SEQUENCE: 9

Arg Trp Tyr Arg
1

<210> SEQ ID NO 10
<211> LENGTH: 4
<212> TYPE: PRT
<213> ORGANISM: Artificial Sequence
<220> FEATURE:
<223> OTHER INFORMATION: Novel Sequence

<400> SEQUENCE: 10

Arg Trp Ile Arg
1

<210> SEQ ID NO 11
<211> LENGTH: 4
<212> TYPE: PRT
<213> ORGANISM: Artificial Sequence
<220> FEATURE:
<223> OTHER INFORMATION: Novel Sequence

<400> SEQUENCE: 11

Arg Trp Leu Arg
1

<210> SEQ ID NO 12
<211> LENGTH: 4
<212> TYPE: PRT
<213> ORGANISM: Artificial Sequence
<220> FEATURE:
<223> OTHER INFORMATION: Novel Sequence

<400> SEQUENCE: 12

Arg Trp Pro Arg
1

<210> SEQ ID NO 13
<211> LENGTH: 4
<212> TYPE: PRT
<213> ORGANISM: Artificial Sequence
<220> FEATURE:
<223> OTHER INFORMATION: Novel Sequence

<400> SEQUENCE: 13

Arg Trp Val Arg
1

<210> SEQ ID NO 14
<211> LENGTH: 4
<212> TYPE: PRT
<213> ORGANISM: Artificial Sequence
<220> FEATURE:
<223> OTHER INFORMATION: Novel Sequence
```

```
<400> SEQUENCE: 14

Arg Trp Cys Arg
1

<210> SEQ ID NO 15
<211> LENGTH: 4
<212> TYPE: PRT
<213> ORGANISM: Artificial Sequence
<220> FEATURE:
<223> OTHER INFORMATION: Novel Sequence

<400> SEQUENCE: 15

Arg Trp Met Arg
1

<210> SEQ ID NO 16
<211> LENGTH: 4
<212> TYPE: PRT
<213> ORGANISM: Artificial Sequence
<220> FEATURE:
<223> OTHER INFORMATION: Novel Sequence

<400> SEQUENCE: 16

Arg Trp Ser Arg
1

<210> SEQ ID NO 17
<211> LENGTH: 4
<212> TYPE: PRT
<213> ORGANISM: Artificial Sequence
<220> FEATURE:
<223> OTHER INFORMATION: Novel Sequence

<400> SEQUENCE: 17

Arg Trp Thr Arg
1

<210> SEQ ID NO 18
<211> LENGTH: 4
<212> TYPE: PRT
<213> ORGANISM: Artificial Sequence
<220> FEATURE:
<223> OTHER INFORMATION: Novel Sequence

<400> SEQUENCE: 18

Arg Trp Asn Arg
1

<210> SEQ ID NO 19
<211> LENGTH: 4
<212> TYPE: PRT
<213> ORGANISM: Artificial Sequence
<220> FEATURE:
<223> OTHER INFORMATION: Novel Sequence

<400> SEQUENCE: 19

Arg Trp Gln Arg
1

<210> SEQ ID NO 20
<211> LENGTH: 4
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
```

```
<222> LOCATION: (3)..(3)
<223> OTHER INFORMATION: Xaa is a naphthylalanine

<400> SEQUENCE: 20

Arg Trp Xaa Arg
1

<210> SEQ ID NO 21
<211> LENGTH: 4
<212> TYPE: PRT
<213> ORGANISM: Artificial Sequence
<220> FEATURE:
<223> OTHER INFORMATION: Novel Sequence

<400> SEQUENCE: 21

Arg Trp His Arg
1

<210> SEQ ID NO 22
<211> LENGTH: 4
<212> TYPE: PRT
<213> ORGANISM: Artificial Sequence
<220> FEATURE:
<223> OTHER INFORMATION: Novel Sequence

<400> SEQUENCE: 22

Arg Trp Lys Arg
1

<210> SEQ ID NO 23
<211> LENGTH: 4
<212> TYPE: PRT
<213> ORGANISM: Artificial Sequence
<220> FEATURE:
<223> OTHER INFORMATION: Novel Sequence

<400> SEQUENCE: 23

Arg Trp Gly Arg
1

<210> SEQ ID NO 24
<211> LENGTH: 6
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (6)..(6)
<223> OTHER INFORMATION: Xaa is any amino acid

<400> SEQUENCE: 24

Phe Arg Trp Trp His Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (6)..(6)
<223> OTHER INFORMATION: Xaa is any amino acid

<400> SEQUENCE: 25

Arg Arg Trp Trp Met Xaa
```

```
<210> SEQ ID NO 26
<211> LENGTH: 6
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (6)..(6)
<223> OTHER INFORMATION: Xaa is any amino acid

<400> SEQUENCE: 26

Arg Arg Trp Trp Cys Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (6)..(6)
<223> OTHER INFORMATION: Xaa is any amino acid

<400> SEQUENCE: 27

Arg Arg Trp Trp Arg Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Novel Sequence
<220> FEATURE:
<221> NAME/KEY: misc_feature
<222> LOCATION: (6)..(7)
<223> OTHER INFORMATION: Xaa is any amino acid

<400> SEQUENCE: 28

Arg Arg Trp Trp Cys Xaa Xaa
1               5

<210> SEQ ID NO 29
<211> LENGTH: 4
<212> TYPE: PRT
<213> ORGANISM: Artificial Sequence
<220> FEATURE:
<223> OTHER INFORMATION: Novel Sequence

<400> SEQUENCE: 29

Arg Phe Phe Arg
1

<210> SEQ ID NO 30
<211> LENGTH: 5
<212> TYPE: PRT
<213> ORGANISM: Artificial Sequence
<220> FEATURE:
<223> OTHER INFORMATION: Novel Sequence

<400> SEQUENCE: 30

Arg Trp Phe Arg Arg
1               5
```

```
<210> SEQ ID NO 31
<211> LENGTH: 4
<212> TYPE: PRT
<213> ORGANISM: Artificial Sequence
<220> FEATURE:
<223> OTHER INFORMATION: Novel Sequence

<400> SEQUENCE: 31

Arg Phe Trp Arg
1

<210> SEQ ID NO 32
<211> LENGTH: 4
<212> TYPE: PRT
<213> ORGANISM: Artificial Sequence
<220> FEATURE:
<223> OTHER INFORMATION: Novel Sequence

<400> SEQUENCE: 32

Trp Arg Trp Phe
1
```